United States Patent
Liao et al.

(10) Patent No.: US 9,194,005 B2
(45) Date of Patent: Nov. 24, 2015

(54) METHODS AND BIOMARKER FOR EVALUATING CANCER METASTASIS, PHARMACEUTICAL COMPOSITION FOR INHIBITING CANCER METASTASIS, AND METHOD FOR ANALYZING SECRETOME

(71) Applicant: National Cheng Kung University, Tainan (TW)

(72) Inventors: Pao-Chi Liao, Tainan (TW); Ying-Hwa Chang, Taipei (TW); Shu-Hui Lee, Changhua County (TW); Hua-Chien Chang, Tainan (TW); Yau-Lin Tseng, Tainan (TW); Wu-Wei Lai, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 25 days.

(21) Appl. No.: 14/028,861

(22) Filed: Sep. 17, 2013

(65) Prior Publication Data

US 2014/0120528 A1    May 1, 2014

(30) Foreign Application Priority Data

Oct. 31, 2012    (TW) .............................. 101140274 A

(51) Int. Cl.
   *C12N 15/113*    (2010.01)
   *C12Q 1/68*    (2006.01)
   *G01N 33/574*    (2006.01)

(52) U.S. Cl.
   CPC ........ *C12Q 1/6886* (2013.01); *G01N 33/57423* (2013.01); *C12Q 2600/118* (2013.01); *C12Q 2600/158* (2013.01); *G01N 2570/00* (2013.01)

(58) Field of Classification Search
   None
   See application file for complete search history.

(56) References Cited

U.S. PATENT DOCUMENTS

2005/0137155 A1 *    6/2005    McSwiggen et al. ........... 514/44

OTHER PUBLICATIONS

Eltoweissy et al, Proteomics analysis identifies PARK7 as an important player for renal cell resistance and survival under oxidative stress, published online Feb. 2011, Mol.BioSyst., 7: 1277-88.*

* cited by examiner

*Primary Examiner* — Tracy Vivlemore
*Assistant Examiner* — Kate Poliakova-Georgantas
(74) *Attorney, Agent, or Firm* — Bacon & Thomas, PLLC

(57) ABSTRACT

The invention relates to methods and biomarker for evaluating cancer metastasis, pharmaceutical composition for inhibiting cancer metastasis, and method for analyzing secretome. By combining a hollow fiber cartridge (HFC) culture system with quantitative proteomics technology, cancer metastasis-related secrectomes can be found. Furthermore, this is the first time to use PARK7 as a biomarker for judging the process of non-small cell lung cancer.

1 Claim, 16 Drawing Sheets

METHODS AND BIOMARKER FOR EVALUATING CANCER METASTASIS, PHARMACEUTICAL COMPOSITION FOR INHIBITING CANCER METASTASIS, AND METHOD FOR ANALYZING SECRETOME

BACKGROUND OF THE INVENTION

1. Field of the Invention

The present invention relates a method for evaluating lung cancer metastasis, a biomarker for evaluating lung cancer metastasis, a siRNA compound for inhibiting lung cancer metastasis, and a method for analyzing secretome.

2. Description of Related Art

Cancer, also known as malignant neoplasm, is a disease involving failed mechanism of cell growth proliferation. Lung cancer is the most common cause of cancer death in the world, and some remarkable problems that get in the way of treating lung cancer are that there is low abundance of effective prognosis tools, and low abundance of prevention-oriented treatment methods for keeping off metastasis. In terms of the most popular type of occurring cancer by number of patients, non-small cell lung cancer (NSCLC) accounts for approximately 85% of the demographics, and among all the histological types of NSCLC, lung adenocarcinoma is the most common type. Many lung cancer patients are diagnosed with distant metastatic, and most of them die as a result of the metastases instead of due to the original tumors. The survival rate of lung cancer patients within a 5 year time frame during treatment period is 15.2% and only 2.8% for lung cancer patients complicated by distant metastases. Metastasis is clearly a fatal condition adversely affecting malignant tumor development. Unfortunately, current technologies in clinical practice cannot keep up to solve this problem as there is still low abundance of effective diagnostic and prognostic tools for metastasis and other progression predictions. To further increase patients' survival rates, studies related to the mechanisms of metastasis are of immediate importance.

Metastasis, the ultimate event in a cancer progression, can be described as the complex process in which cancer cells travel from a tumor site and migrate through the bloodstream or lymphatic system to other parts of the body. During this intricate process, numerous proteins are required to assist in the progression of the tumor cells. For example, secretory proteins, which are released from cells via various pathways, including the classical ER-golgi pathway, vesicle release, or a specific channel, are known as the secretome. In previous research, cell secretome was widely used via proteomics technologies in cancer research. There are three main aspects of this research, including discovering clinical biomarker, understanding mechanisms of cancer progression, and planning cancer treatment strategy. Previously, there are many studies reporting that some biomarkers are associated with cancer metastasis and aggression and angiogenesis, such as the proteinase MMP-9 and VEGF respectively.

However, modern technology and the discovered biomarkers still have their shortcomings for cancer metastasis and cancer development process prediction. Therefore, there is still room for people in the art to develop and improve prediction accuracy as well as technical aspects.

SUMMARY OF THE INVENTION

An object of the present invention is to provide a method for evaluating lung cancer metastasis, comprising: (A) providing a specimen sample of a subject, wherein the specimen sample comprises a normal tissue and a tumor tissue to be tested; (B) testing expressions of a biomarker in the normal tissue and in the tumor tissue that is pending to be tested respectively, wherein the biomarker is a genotype or a protein of Parkinson disease type 7 (PARK7); (C) comparing the expressions of the biomarker in the normal tissue and the tumor tissue that is pending to be tested, wherein when the expression of the biomarker in the tumor tissue that is pending to be tested is less than that in the normal tissue, it indicates that the subject is subjected to a cancer metastasis risk.

In the step (A), the tumor tissue may be, for example, cell tissue, blood, body fluid or protein, but the tumor tissue for the present invention is not limited thereto.

Particularly, in the step (B), mRNA expression, protein expression, protein derivative expression, or peptide chain expression of proteins of PARK7 in the normal tissue and the tumor tissue to be tested were tested respectively.

Preferably, in the step (B), protein expression of PARK7 in the normal tissue and the tumor tissue to be tested were tested respectively.

In the method for evaluating lung cancer metastasis of the present invention, wherein, protein expression of PARK7 in the normal tissue and the tumor tissue to be tested are tested respectively by enzyme-linked immunosorbent assay (ELISA), immunohistochemistry (IHC), immunoprecipitation (IP), or mass spectrometry (MS).

In the method for evaluating lung cancer metastasis according to the present invention, the lung cancer particularly refers to non-small cell lung cancer (NSCLC).

The present invention also provides a biomarker for evaluating lung cancer metastasis, which may be a nucleotide sequence of PARK7, a complementary strand of the nucleotide sequence of PARK7, a derivative of an oligonucleotide sequence of PARK7, a protein sequence of PARK7, a derivative of the protein sequence of PARK7, a fragment of the protein sequence of PARK7, a variant of the protein sequence of PARK7, or an antibody corresponding to the protein sequence of PARK7.

Particularly, the biomarker for evaluating lung cancer metastasis according to the present invention is a protein sequence of PARK7, a derivative of the protein sequence of PARK7, a fragment of the protein sequence of PARK7, a variant of the protein sequence of PARK7, and an antibody corresponding to the protein sequence of PARK7.

The biomarker PARK7 for evaluating lung cancer metastasis according to the present invention may serve as a biomarker for cancer risk assessment, cancer diagnosis, and cancer progression prediction, wherein the nucleotide sequence of PARK7 is a sequence represented by SEQ ID NO: 1.

In the case of the biomarker for evaluating lung cancer metastasis according to the present invention, the protein sequence of PARK7 is a sequence represented by SEQ ID NO: 2.

Another object of the present invention is to provide an siRNA compound for inhibiting lung cancer metastasis, comprising a target sequence selected from a gene of PARK7.

Particularly, the target sequence comprises 20-25 oligonucleotides.

Particularly, the nucleotide sequence of PARK7 is a sequence represented by SEQ ID NO: 1.

Another object of the present invention is to provide a method for analyzing secretome, comprising the following steps: (A) providing a hollow fiber cartridge (HFC) culture system comprising one or a plurality of hollow fiber cartridges (HFC), a circulation pump, a culture medium supply unit, and a discharge unit, wherein two opposite ends of the circulation pump are connected to the hollow fiber cartridges and the culture medium supply unit respectively; two opposite ends of the hollow fiber cartridges are connected to the circulation pump and the discharge unit respectively; culture medium in the culture medium supply unit is supplied to the hollow fiber cartridges by the circulation pump, and the culture medium flowing through the hollow fiber cartridges is discharged by the discharge unit; (B) culturing a cell pending to be analyzed in the hollow fiber cartridge (HFC) culture system, wherein the cell to be analyzed is cultured on the hollow fiber cartridges; (C) collecting secretomes secreted by the cell to be analyzed; and (D) purifying the secretomes and analyzing protein types thereof before comparing the obtained protein types against a proteome database.

The HFC culture system can provide a three-dimensional (3D) space and a circulating environment for cell growth. The hollow fiber cartridge (HFC) culture system is a non-stationary system, it operates to employ the high surface area of the HFC to emulate a three-dimensional intra-body environment to grow cells, lending itself to improve cell growth. This system allows cell metabolite to be discharged, which effects decrease of cell mortality, and obtainment of sufficient amount of the secretomes by way of small-volume sampling, which helps analysis of the secretomes.

According to the method for analyzing secretome of the present invention, particularly, in the step (D), the secretomes is analyzed by liquid chromatography coupled with tandem mass spectrometry (LC-MS/MS).

In the method for analyzing secretome of the present invention, in the step (D), purifying the secretomes and discretionally marking the secretomes, to analyze the protein types thereof.

In the event that the secretomes is not marked, protein in the secretomes is analyzed for the protein's m/z, charge, and retention time.

In addition, in the method for analyzing secretome of the present invention, the culture medium for the hollow fiber cartridge (HFC) culture system is a serum-free medium (SFM) or a serum medium. In the interest of avoiding serum contamination or serum replacement from factoring into cell growth, serum-free medium is preferred or serum replacement from factoring into cell growth, serum-free medium is preferred.

DETAILED DESCRIPTION OF THE PREFERRED EMBODIMENT

Hereinafter, preferred embodiments of the present invention will be described in detail with reference to the accompanying drawings. However, the present invention is not limited to the embodiments disclosed below, but can be implemented in various forms. The following embodiments are described in order to enable those of ordinary skill in the art to embody and practice the present invention, and those skilled in the art will appreciate that various modifications, additions and substitutions are possible without departing from the scope and spirit of the invention as disclosed in the accompanying claims.

Figure 2:
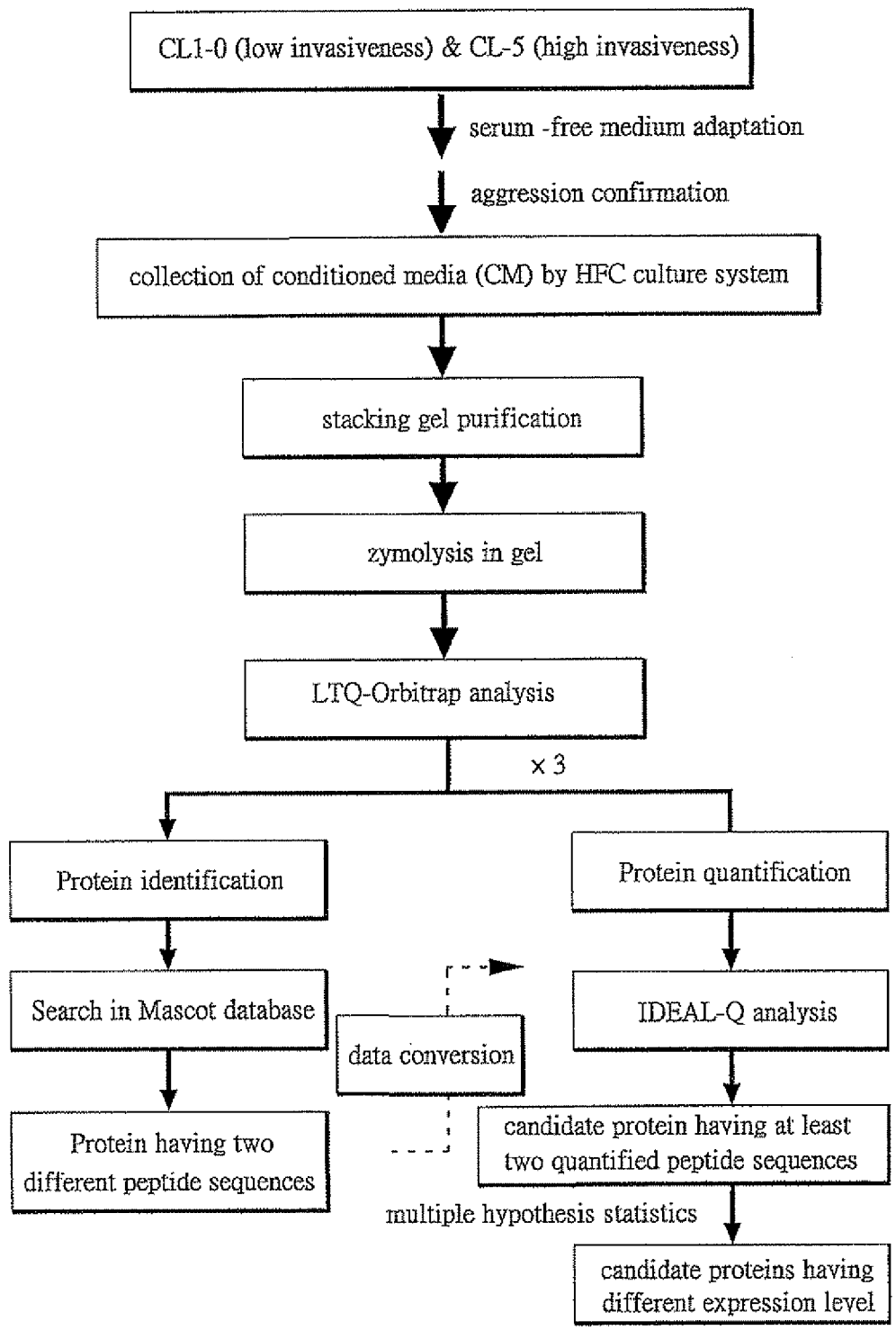
FIG. 2 shows the experimental workflow of secretomes analyses for lung adenocarcinoma metastasis according to an example of the present invention.

Hereinafter, the lung adenocarcinoma cell line will be used as an example to describe a specific embodiment of the present invention in detail, and reference to the flow chart (FIG. 2) is required so the present invention can be more easily understood and applied.

Figure 1A:
FIG. 1A shows the micrographs (200×) of the morphologies of the CL1-0 and CL1-5 cells before and after serum-free medium (SFM) adaptation, which were observed by a microscope (200×).
Figure 1A:
Figure 1A:
Figure 1A:
Figure 1B:
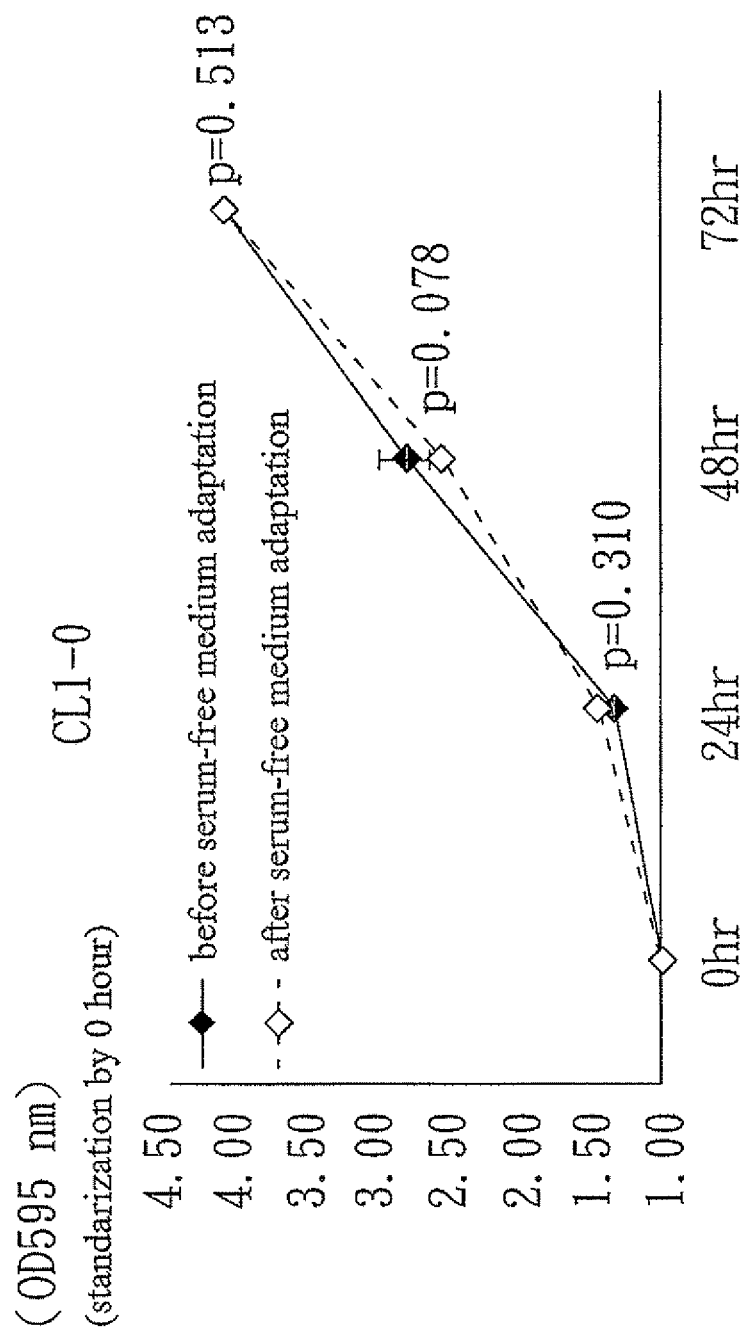
FIG. 1B shows the proliferation of the CL1-0 cells before and after serum-free medium (SFM) adaptation, which was investigated via MTT assay.
Figure 1C:
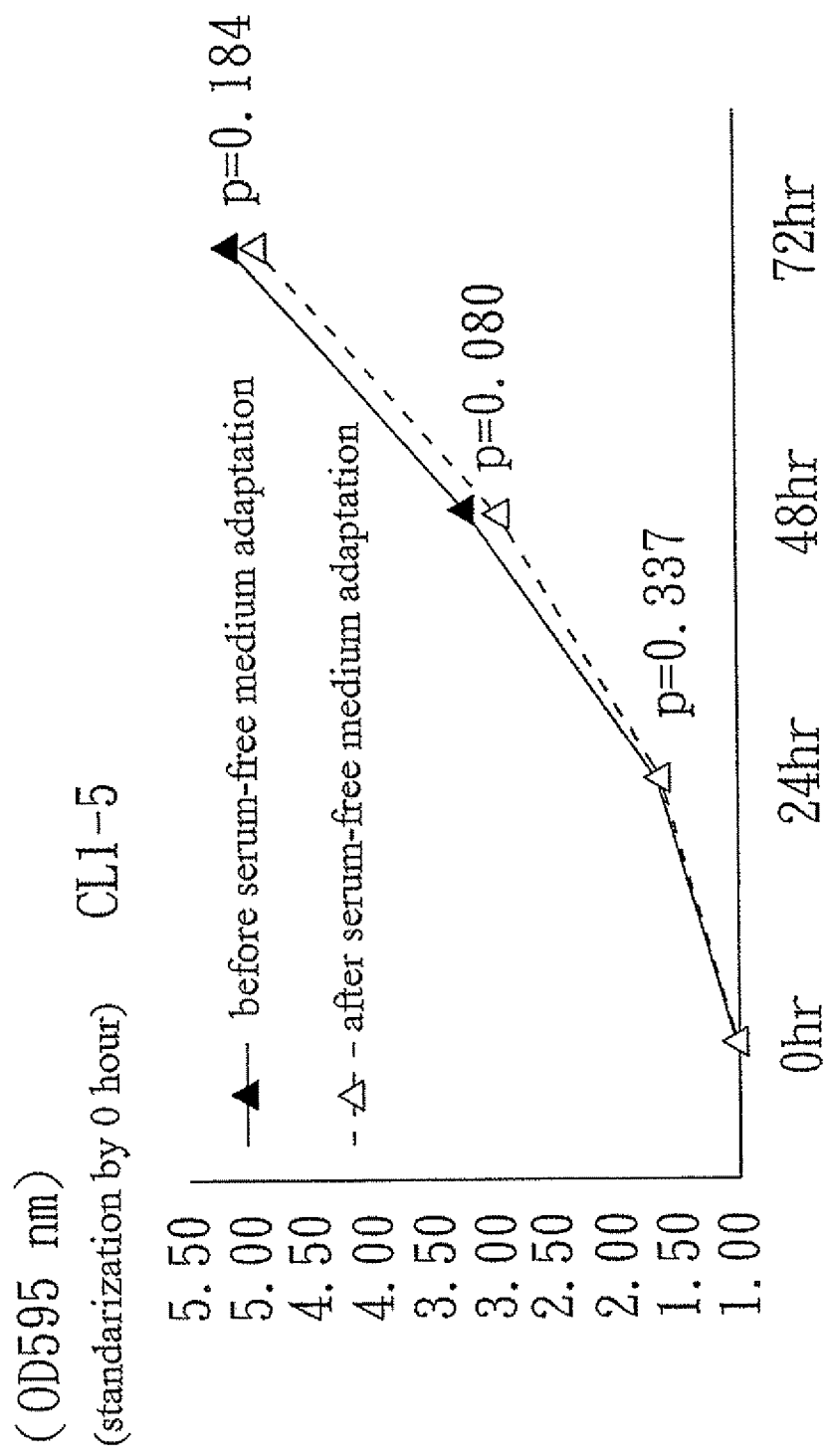
FIG. 1C shows the proliferation of the CL1-5 cells before and after serum-free medium (SFM) adaptation, which was investigated via MTT assay.

Harvesting Conditioned Media from CL1 Cancer Cell Lines Using a Hollow Fiber Cartridge (HFC) Culture System In this example, the lung adenocarcinoma cell lines CL1-0 (lowly invasive) and CL1-5 (highly invasive) derived from the same parental cell line with low and high invasive abilities respectively were provided and cultured in RPMI-1640 media supplemented with 10% fetal bovine serum (FBS). The volume of serum medium was slowly reduced and replaced with serum-free medium consisting of RPMI 1640 with 15% CDM-HD serum replacement and 1% antibiotics. Following 2-3 passages, the morphologies of cell lines CL1-0 and CL1-5 (FIG. 1A) were observed with a microscope (200×), and the cell growth status was tested by MTT technology, referring to FIGS. 1B, 1C. Our results demonstrated that the morphologies and growing conditions for the CL1-0 and CL1-5 cells did not change significantly after SFM adaptation, compared to cells grown in serum medium. After that, the adapted cells were transferred to hollow fiber cartridge (HFC) culture system.

Next, CL1-0 and CL1-5 cells (~5×10$^7$) were suspended in serum-free medium then inoculated into the extra-capillary space (ECS) of the hollow fiber cartridge. 15 mL of secretome samples in conditioned media (CM) from the extra-capillary space (ECS) of the hollow fiber cartridge (HFC) culture system were collected every 24 hrs. The media used for maintaining cell growth was refreshed every day. In addition, glucose and lactate concentrations were also measured daily to monitor cell growth in the hollow fiber cartridge (HFC) culture system.

CM harvested from the ECS of the hollow fiber cartridge (HFC) culture system was ultracentrifuged at 10000×g for an hour to remove cell debris. Then, the protein concentrations of the secretome samples were determined using the Bradford assay (Bio-Rad, Hercules, Calif., USA).

Figure 3:
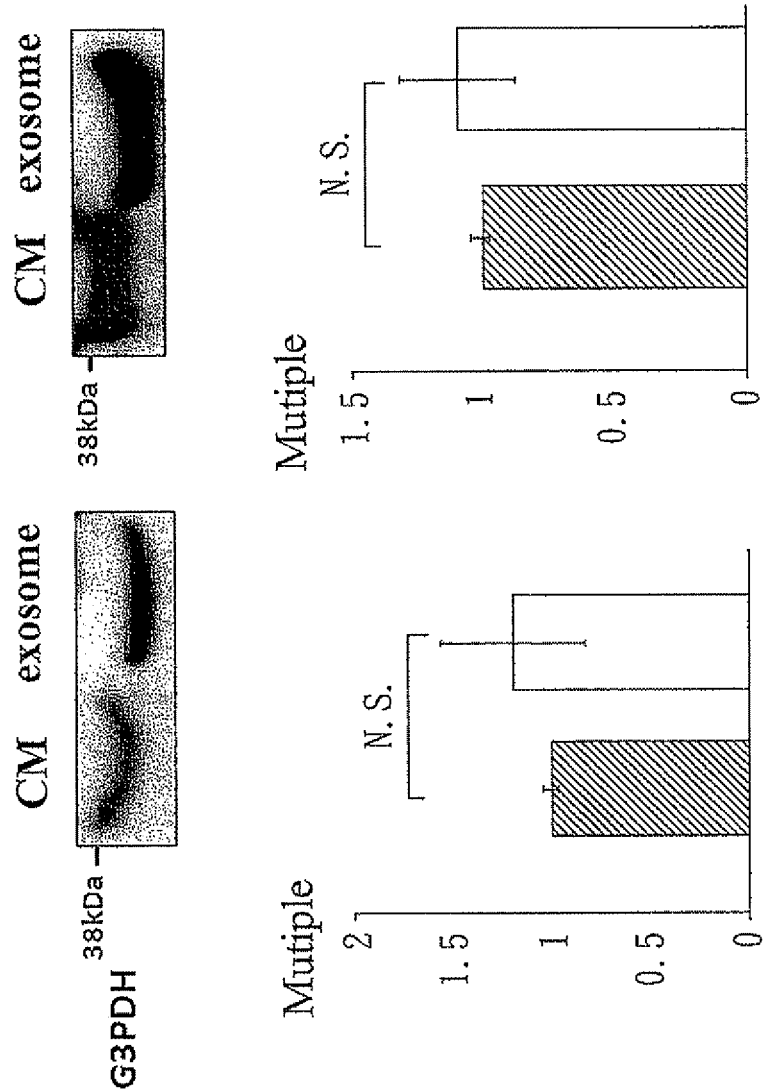
FIG. 3 shows different expression levels of the housekeeping protein G3PDH with and without exosome purification in an identical amount of CM.

In order to confirm that the intracellular proteins were come from the cell secretion rather than via cell lysis, a total of 100 m of CM sample was equally separated into two parts. One of the CM parts was used for exosome purification, to be compared against the housekeeping protein G3PDH between the CM samples (50 μg) applied to exosome purification and another CM part (50 μg). Referring to FIG. 3, the G3PDH protein appeared in similar amounts between the CM sample (50 μg) and exosome fraction. These results confirm that intracellular proteins were released into the extracellular space via exosome secretion.

Sample Purification and Analysis

The stacking gel-aided purification method was previously established in the conventional knowledge for use in secretome sample clean-up, wherein the CM samples were mixed with the sample dye and 0.5 M DTT before being added into a self-poured stacking gel that contained 50% running gel and a 4% stacking gel. Then, SDS-PAGE was performed at 55 V for 30 min. The protein samples were stacked to the border between the stacking and running gel.

In this example, the CM samples during the second to tenth day of cell growth were collected, and then the protein in the CM sample of CL1-0 and CL1-5 CM cells were recovered using the stacking gel-aided purification method for uses in subsequent experiments of staining and hydrolyzing colloid into peptide fragments.

Coomassie Brilliant Blue R-250 was used to stain the gel. All bands were excised and digested in-gel with trypsin. The gel pieces were reduced with 0.5 M DTT (56° C.) and alkylated with saturated iodoacetamide at room temperature, with each step requiring 1 hr.

20 μL of 0.1 μg/μL of modified trypsin was added to the gel pieces, and they were incubated overnight at 37° C. The digested peptide samples were purified with a C18 tip followed by mass spectrometry analyses.

Mass Spectrometry Analyses

In the present example, the MS samples of CL1-0 and CL1-5 CM cells were analyzed using a LTQ-Orbitrap hybrid mass spectrometer with a nanoelectrospray ion source (Nano-electrospray, branded under ThermoElectron, San Jose Calif.) coupled to a nano flow HPLC (Nanoflow HPLC, branded under Agilent Technologies 1200 series).

Protein Identification and Quantification

In the protein identification of the present example, searching with the Mascot database search was performed, and a protein was selected if it had at least two unique peptide sequences that could be quantified, where in the two peptide sequence defined as RANK 1 are the candidate protein of the present invention. A total of 412 and 531 proteins were identified in CL1-0 and CL1-5 cells, respectively. Subsequently, identified proteins were quantified via IDEAL-Q software.

Next, protein quantification was performed in terms of the candidate protein's m/z, charge, and retention time in the LC-MS/MS analysis, using IDEAL-Q software. By means of this method, a total of 50 candidate proteins were identified with different levels between CL1-0 and CL1-5 cell lines. Among these proteins, 25 and 25 proteins exhibited high levels in the CL1-0 and CL1-5 cells, respectively.

Selection of Protein Candidates Via Interactome Analysis

Next, interactions between the 50 candidate proteins were analyzed using the STRING 9.0 database and 7 proteins were selected based on these results. The proteins ACTN4, FN1, PARK7, PRDX4 and GRP78 within the highly invasive CL1-5 cells were expressed at high levels, and proteins MYO6 and GSR within the lowly invasive CL1-0 cells were expressed at high levels.

Figure 4:
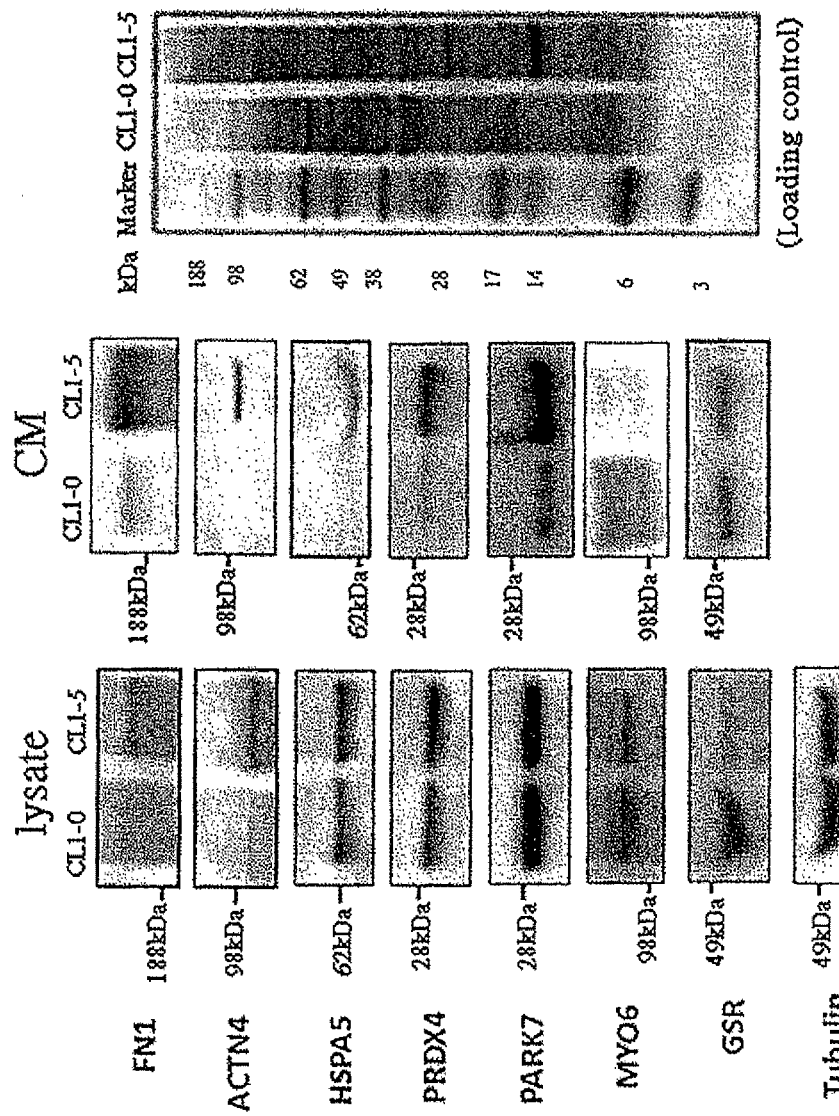
FIG. 4 shows the comparison of candidate protein expressions in CL1-0 and CL1-5 via Western blot according to an example of the present invention.

In this example, as shown in FIG. 4, the 7 protein levels were further analyzed via western blot (the housekeeping protein tubulin as a control). The findings produced by the western blot analysis and the mass spectrometry data were compared against each other to analyze for consistency.

In this case, the results of PARK7 from the western blot analysis and from the mass spectrometry PARK7 were consistent with each other, this confirms that PARK7 has high levels of expression in CL1-5 cells.

Figure 5A:
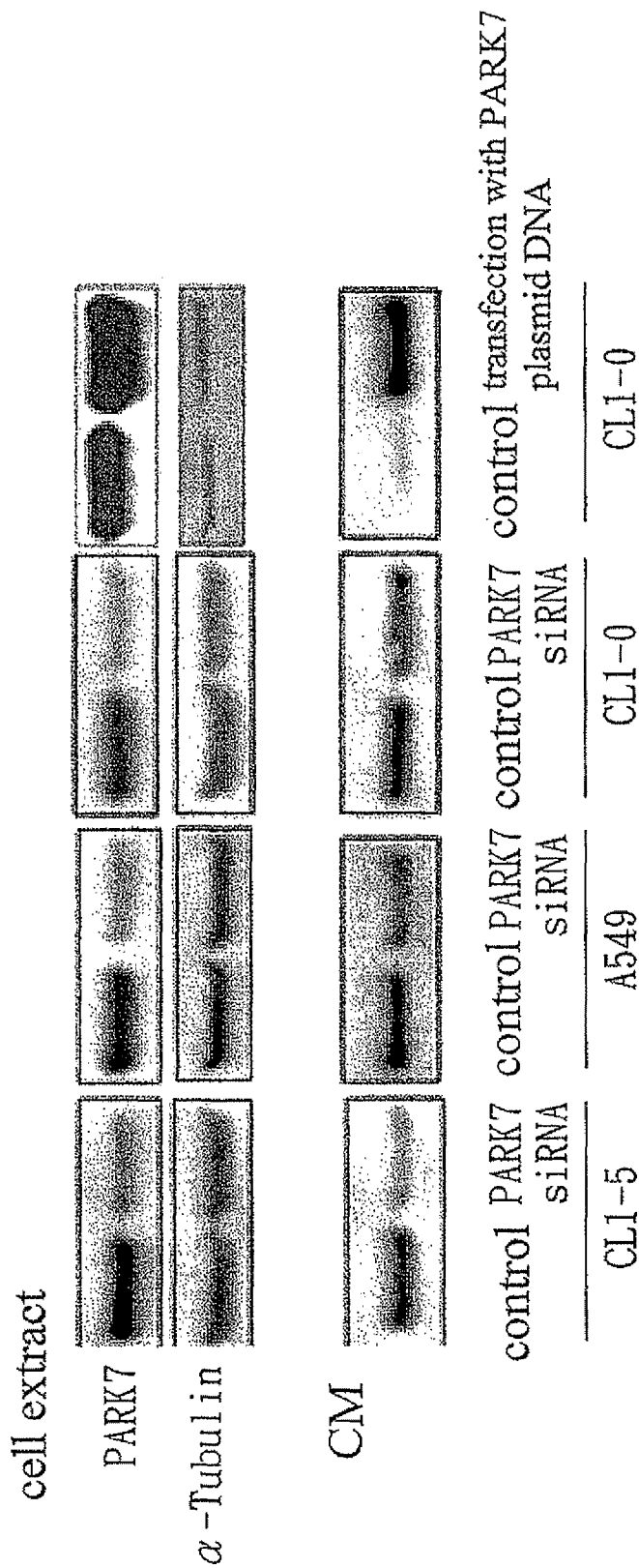
FIG. 5A shows the PARK7 protein expressions in cells treated with PARK7 siRNA or the plasmids transfected with PARK7 DNA according to an example of the present invention.
Figure 5B:
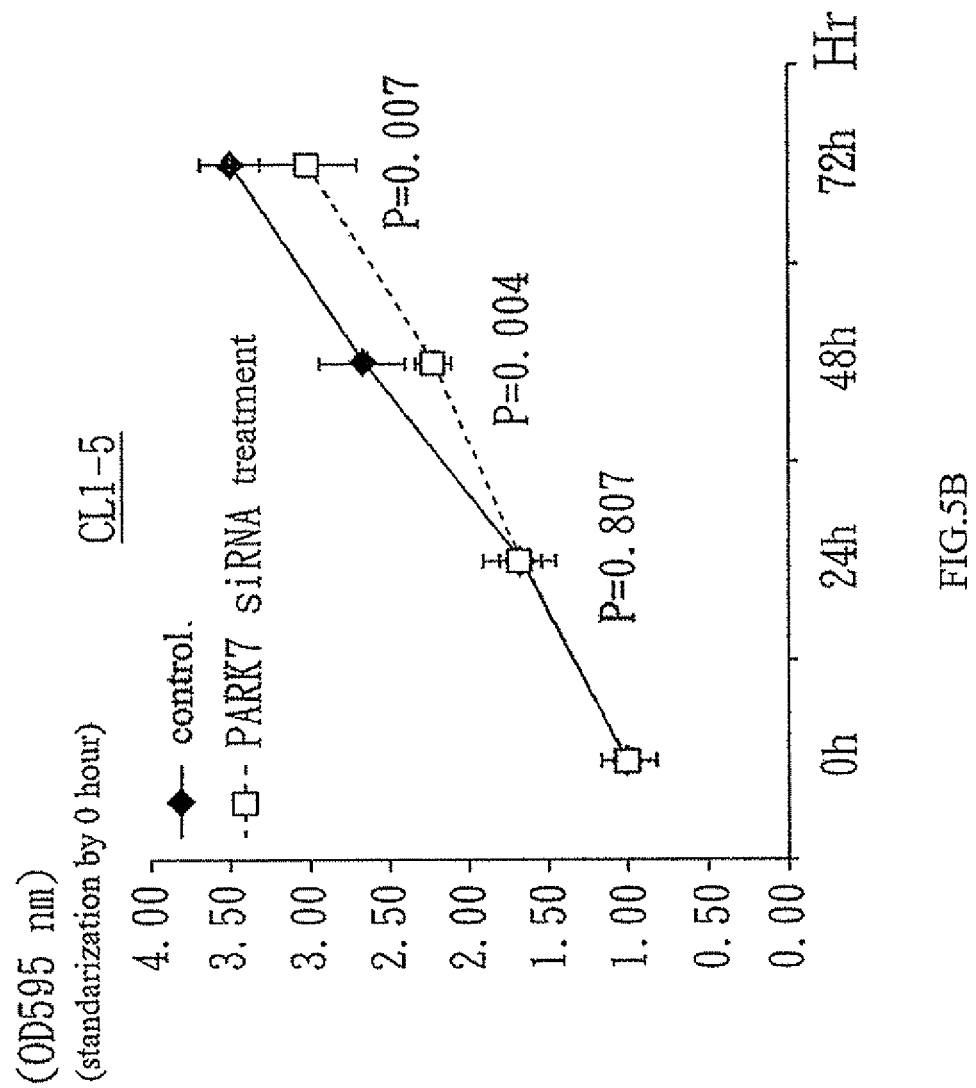
FIG. 5B shows the proliferation of the CL1-5 cell line treated with PARK7 siRNA according to an example of the present invention.
Figure 5C:
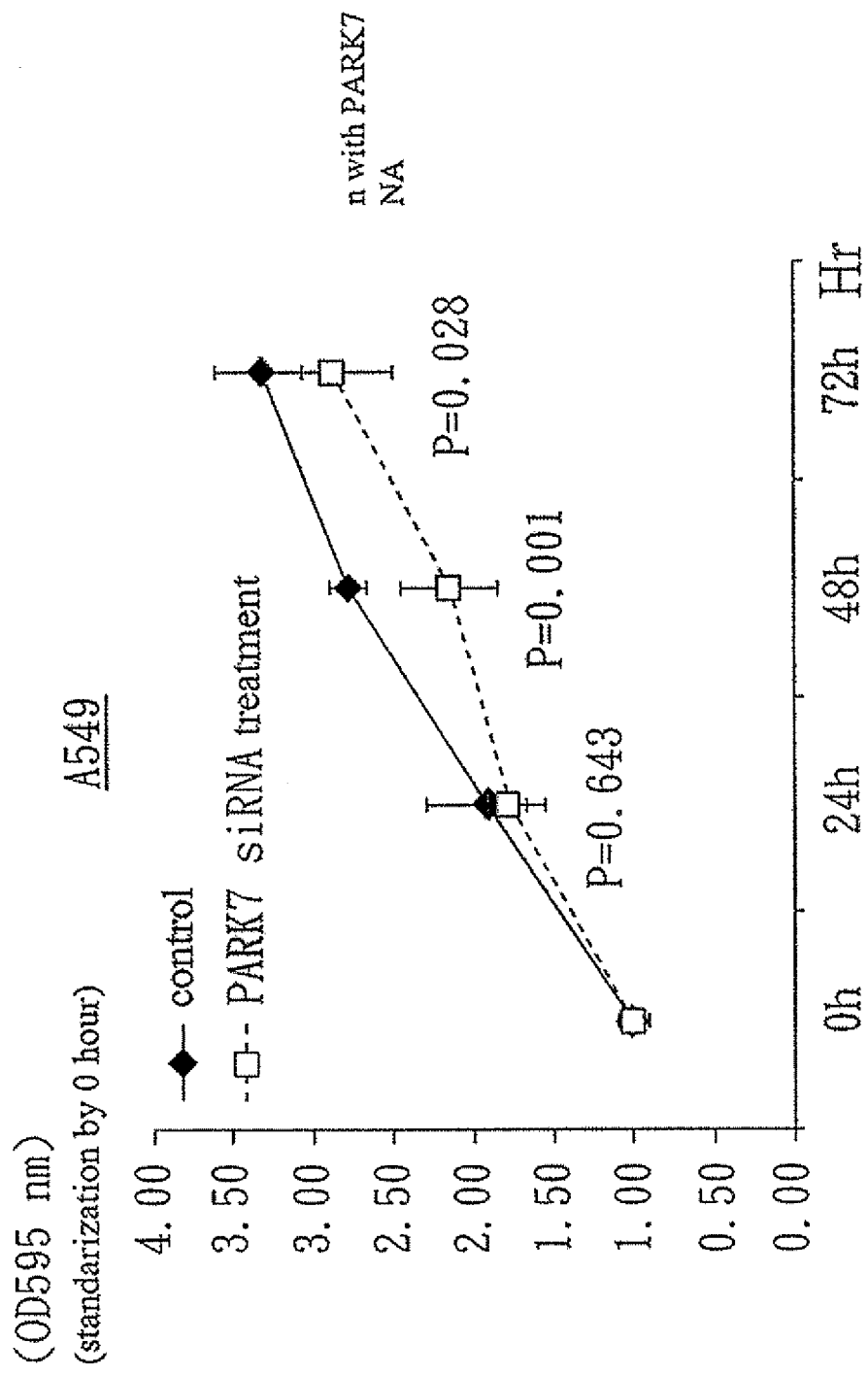
FIG. 5C shows the proliferation of the A549 cell line treated with PARK7 siRNA according to an example of the present invention.

PARK7's Significant Impact on Cell Proliferation, Migration/Invasiveness in Lung Adenocarcinoma Cells To further verify the PARK7's potential related to metastasis-associated functions and service as a biological marker, in the present example, the A549 cells were additionally employed for test. As shown in FIG. 5, first, CL1-5, A549 and CL1-0 cells were treated with PARK1 siRNA respectively. The siRNA of PARK7 was purchased from Santa Cruz Biotechnology (Santa Cruz, Calif., USA). The sequence of the siRNA was the sc-37080A sense: CUCCACUUGUUCU-UAAAGATT (SEQ ID NO: 3) and antisense: UCUUUAA-GAACAAGUGGAGTT (SEQ ID NO: 4), sc-37080B sense: CGACGAUCACUUAGAGAAATT (SEQ ID NO: 5), and antisense: UUUCUCUAAGUGAUCGUCGTT (SEQ ID NO: 6), sc-37080C sense: GGAAGUAUGGAAGUCA-CAATT (SEQ ID NO: 7), and antisense sc-37080C:UU-GUGACUUCCAUACUUCCTT (SEQ ID NO: 8), and compared against scrambled siRNA which served as the control. As shown in FIG. 5A, first, the level of the PARK7 protein expression in the cell lines having plasmids treated with PARK7 siRNA or transfected with PARK7 DNA was confirmed, to ensure that siRNA successfully inhibits PARK7 performance in the cells, or the level of the PARK7 protein expression was increased due to the plasmids transfected with PARK7 DNA.

The results of MTT assay indicated that with the reduced synthesis and secretion of PARK7 in CL1-5 (FIG. 5B) and A549 (FIG. 5C), cell proliferation was significantly reduced.

Figure 5D:
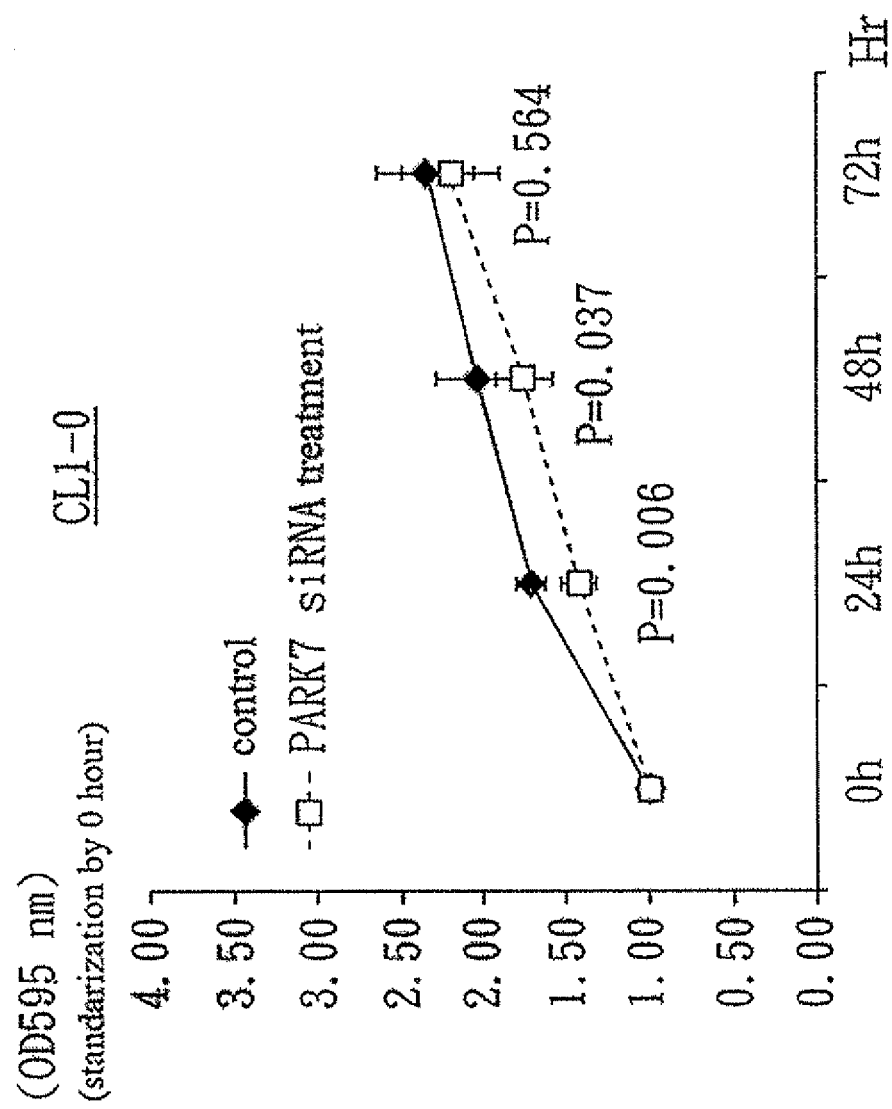
FIG. 5D shows the proliferation of the CL1-0 cell line treated with PARK7 siRNA according to an example of the present invention.
Figure 5E:
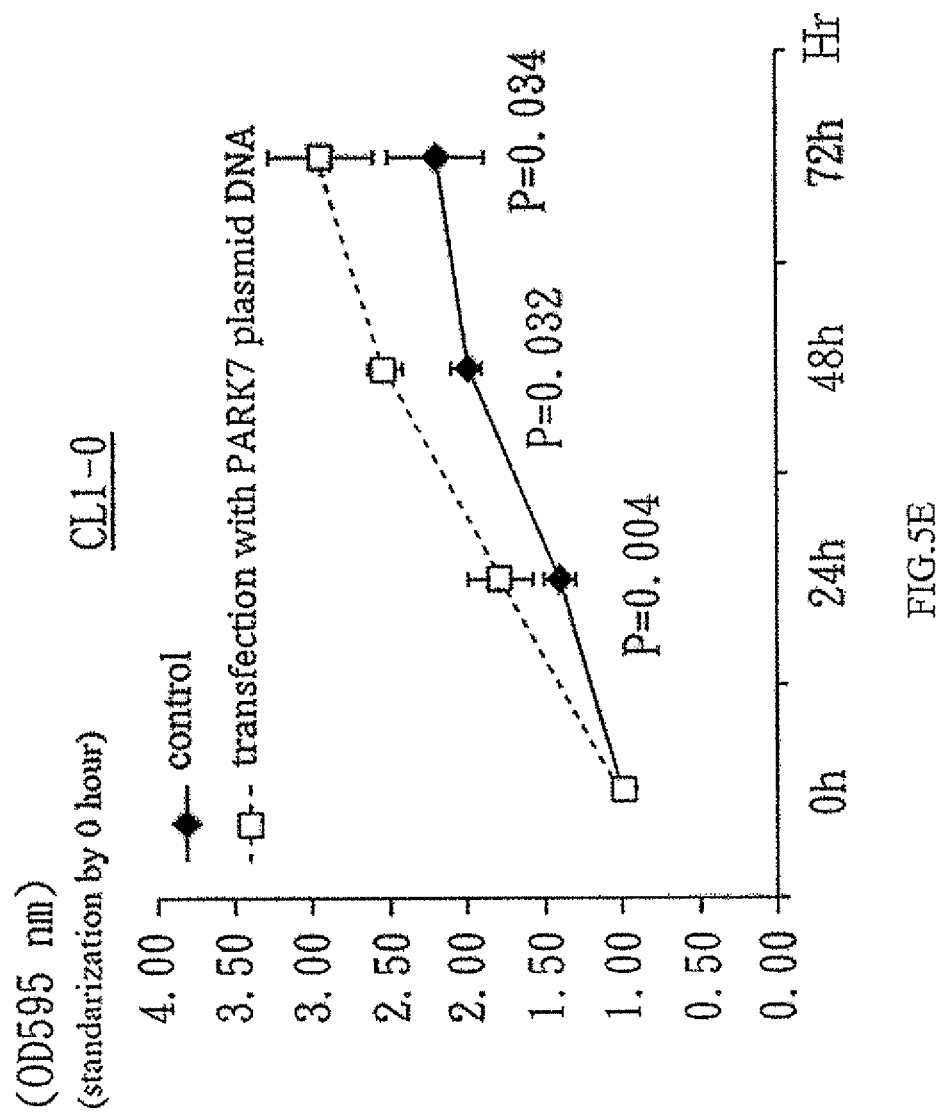
FIG. 5E shows the proliferation of the CL1-0 cell line treated with the plasmids transfected with PARK7 DNA according to an example of the present invention.

According to the results of MTT assay, the proliferation of CL1-0 treated with PARK7 siRNA was also influenced and was reduced slightly (FIG. 5D). Further, CL1-0 was transfected respectively into empty plasmids (control group) and plasmids carrying PARK7 DNA. The results of MTT assay shown that CL1-0 cell transfected with the plasmids carrying PARK7 DNA CL1-0 grew better compared to the control (FIG. 5E).

Figure 5F:
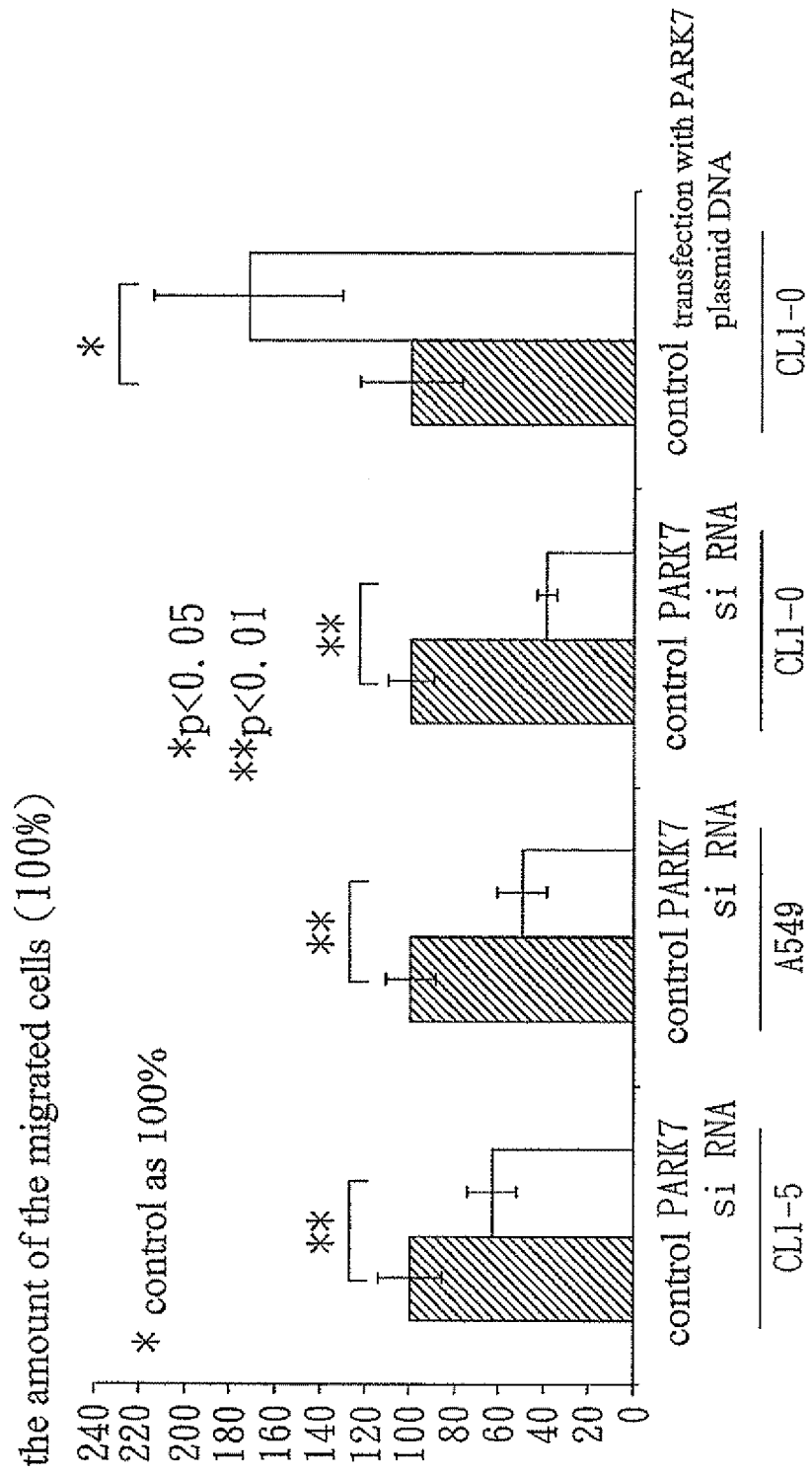
FIG. 5F shows the amount of the migrated CL1-5, A549 and CL1-0 cells respectively in each region according to an example of the present invention.

In addition, FIG. 5F shown that the migration of CL1-5 and A549 cell lines were greatly reduced due to the treatment with PARK7 siRNA. In the case of lowly invasive CL1-0, it was also found that the cell growth and migration were reduced when the expression of PARK7 protein decreased. Conversely, the growth and migration of lowly invasive CL1-0 cell line were promoted when PARK7 was over-expressed.

Clinical Expression of PARK7 in Tissue Specimen and Plasma

Figure 6A:
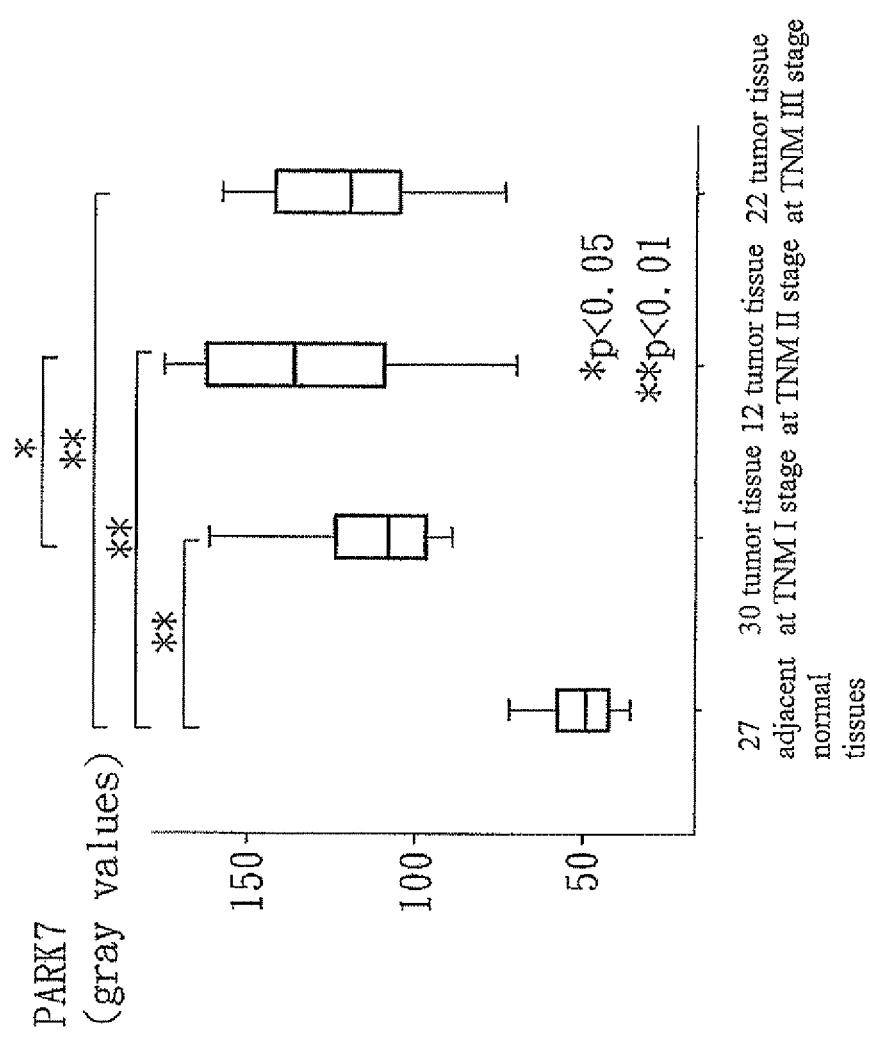
FIG. 6A shows the expression levels of PARK7 between adjacent normal tissue specimens and cancerous tissues with overall TNM stages I, II, and III, wherein the statistical difference therebetween was obtained.
Figure 6B:
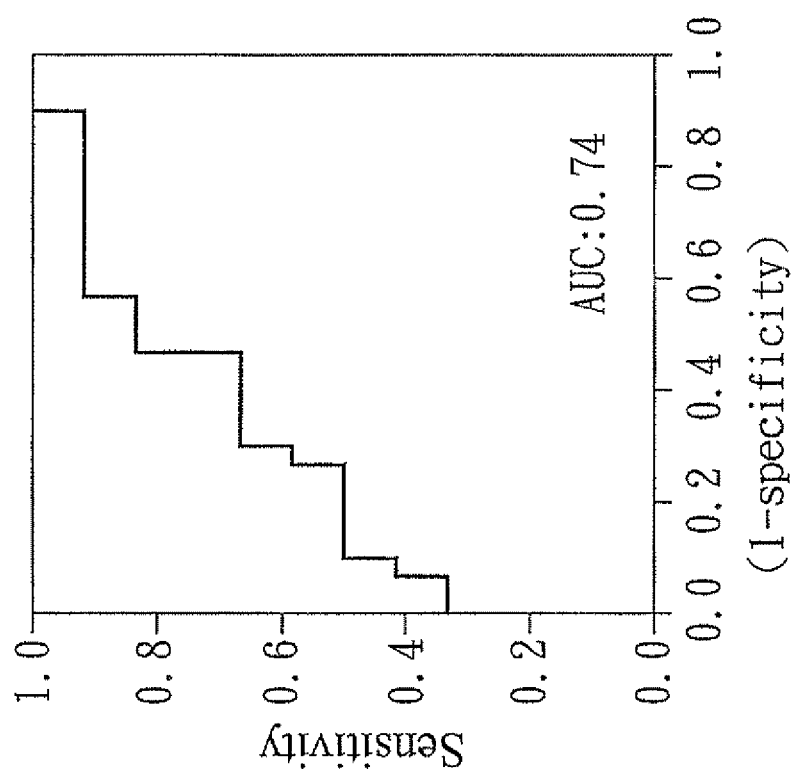
FIG. 6B shows the receiver operating characteristic (ROC) curve according to tissue specimens of the present invention, wherein TNM stages I and II are clearly distinguished.
Figure 6C:
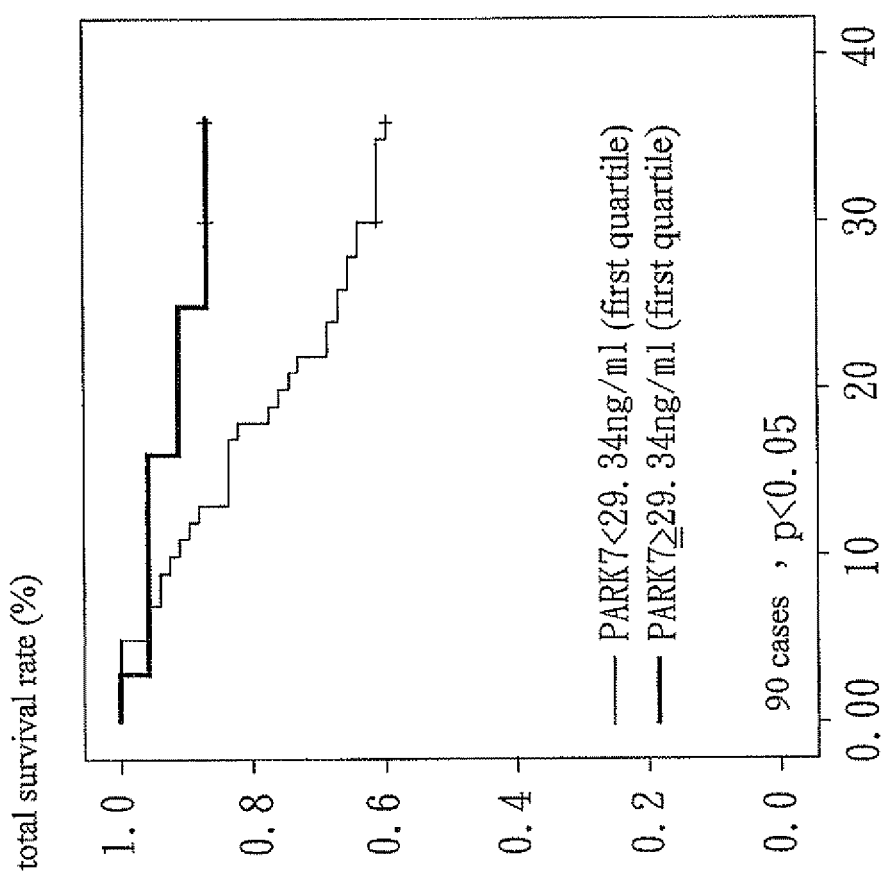
FIG. 6C shows the Kaplan Meier estimator of the survival rates according to the plasma samples of the present invention.
Figure 6D:
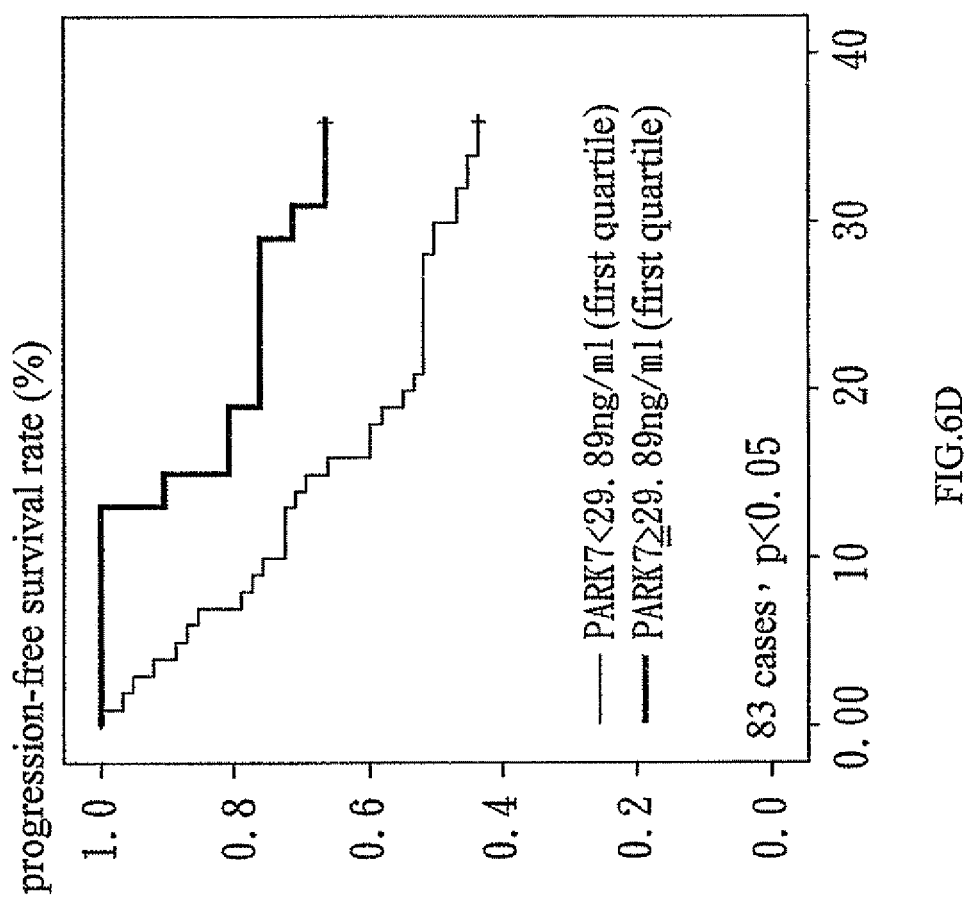
FIG. 6D shows the Kaplan Meier estimator of the progression-free survival rates according to the plasma samples of the present invention.

Next, the clinical expression of PARK7 was confirmed by tissue specimen and plasma. The tissue microarray including 64 cancerous tissues and 31 adjacent normal tissues was used. By international standards, the number of the cancer diagnosis phases is defined in terms of the TNM system embodying different notations including the tumor size (T), regional Lymph Nodes (N), distant Metastasis (M), wherein the level of the PARK7 expression had a high degree of correlation with TNM stage and lymph node metastasis. In addition, as shown in FIG. 6A, the levels of the PARK7 expression in cancerous tissues were significantly higher than that in normal tissues. According to the result of receiver operating characteristic (ROC) curve analysis, the stage I and stage II of the patients were distinguished clearly by the different levels of the PARK7 expression (FIG. 6B). In clinical expression, PARK7 levels within the plasma samples were significantly higher than that in the normal tissue. According to the Kaplan-Meier of FIGS. 6C and 6D, when the cut-off value of PARK7's expression level was within the first quartile, patients with levels within this quartile had 3-year survival and progression-free rates; however, when the cut-off value was below the first quartile, patients with such a level had lower survival rates than patients with levels above this quartile.

What is claimed is:

1. A PARK7 siRNA composition for inhibiting lung cancer metastasis, wherein the composition comprises a mixture of SEQ ID NO: 3, SEQ ID NO: 4, SEQ ID NO: 5, SEQ ID NO: 6, SEQ ID NO: 7, and SEQ ID NO: 8.

* * * * *

SEQUENCE LISTING

```
<160> NUMBER OF SEQ ID NOS: 8

<210> SEQ ID NO 1
<211> LENGTH: 31215
<212> TYPE: DNA
<213> ORGANISM: Homo sapiens

<400> SEQUENCE: 1
ccggaagtgg acctacgtca tgcaggtcag tcggtaggtt tccggcgccc agcgccccgt      60
gggagttgtg tctggtggcc cacgctgggg gggggctctt cacactggtg ggcgcagagg     120
cgaagccgtt cccagggccc ctcacagaac tcggtgtcag aatttccccc cttgcaccag     180
cgccgcctca aatgtcaggg ctcgcccact cttctccggt ctcgccgaca taaccttttg     240
ggggctccag aggggaaatt tgccgtttct gccggaccgc tctagagcgt gcctgaaccc     300
ggcctttatg ggatgttgac agctacgttt attcagtgcc ccagaggcct tctttatgcc     360
cagtaactac aatttaaatt ccttctctgc ttcattttgt agtcgtctgg tgaatttgac     420
gtgagaaata agattaaaat aggaataaga aattagttga aatcacattg tagagttctg     480
caaatgtaaa atattaattt atagcaataa agcaggctgt caaataacag aggatgaaag     540
caggataata cttggtcaga acctgctgta tgccaggggc tgtgacagat gctggggatt     600
cagcaaccac caagacaaga aggttcttcc ggcgttcaca ggactagggg aagacacaat     660
aaataactaa aggcaaaatg ctagaatgat gcgctctctc tcaagatgaa atatagaaca     720
tgatttattt tttattttta ttttattttta ttttgagacg gagtttcgct cttgttgccc     780
aggctggagt gcaatggtgc gatctaggct cactgctacc tccgcttccc gggttcaagc     840
gattctcctg cttcagcctc ccgaaagtag ctgggattac aggtgcctgc cactacgccc     900
ggctaatttt tttgtatttt tagtagagac agggtttccc catgttggcc agggtggtct     960
ggaactccta acctcaggtg atccacccgc ctcggcttcc caaagtgctg ggattacagg    1020
tgtgagccac tgcgcccagc cgagaacgat ttattttaga gtgtttactt aatgagatgc    1080
ctaatgtaag agtgacccat ggaaaaataa taacttggca gcagtttttt ttgccgctaa    1140
gatcaggaca attctgaggg gagttttgtt ttggaacgat gaccagatgg ccatgggtgg    1200
ctattactaa cactgtcaat gccatttctc tgttattgcc ttgtgacctc cacaggcaga    1260
gcaatatttc atcattaaaa gttgcaactg ctatgagaag ctacgttcct tgaaaacaga    1320 gttttttggcc aggaatagtt gcttatgcct gtagttccag ctacttggga ggctgaggca    1380
ggaggatccc ttaagcccag gaggtggagg ccaacctggg caacatagcc aggcccggtc    1440
tctaaaaatg aaataaaacc ggcagttttct tccttcgtac ctcccgcagt gcataaagag    1500
ttgtcaaatg ttgagttaaa aaggtagtgg ataggatggg gcggttctgc ctggaaattg    1560
```

```
gagactgaac taggaagtgt cttcgttgtc agtactacag cagtattttt tggtaaatgg    1620 tttaatttt  tggttttatc ttatgaatgt gtgatgagaa atatgcatga actatagagt    1680
gtcttaagtg taactgactt ttaatattga cagtatatgg tgggtagagt gtgaaattta    1740
gcatcagaaa tctgaatttg accaagactg caggaccta tacagtcatt tcacccttct     1800
ggacctcaac cttcacatcc gtggaaggaa aattgtaaca cctgccagga agtcaatata    1860
taaggtctaa agatgataaa tgagaaataa aatattagca tactgtttca aaatactgat    1920
acactaccag aagaaacagt tgaaagagtt gaaaatactt gcttctgggg agcagggctg    1980
aggggaagga ctgagttaga gggctgctgc tgcatggatt cactactgct ctgtagcaaa    2040
acctggctgc tacagttcac cgttgggttg tagtaactct gtttcaggtt gttagttgtg    2100
caggttggct agggccgctc tgttccacat gttcattctg aaacccaggt tgagggaaca    2160
gcagcaactt gcctggggga aaagctcttc ctacagcaat tcaaaagtag aagagcacaa    2220
cctaataatc agggcagact tttcaaggct ttgttacagg tgtctgttaa cattccatgg    2280
accaaaacaa ggccaaaccc aaaatcaagg gacaggaagt agactccacc catgcaggtg    2340 gaagggagt  gactatttct gaaaaataat ccaatctgcc gcaagtaata cttgactttt    2400
taaaactgtg cagtgtattc acttggtaag aattaatgct gactgtggtc catttcaggt    2460
cttgatggtg atgcgtatgt ctcaggaatg ttaactccag ttcattctct ctggctctca    2520
ctgctgaaac atctgtcatc tttaggctat cgtggctgtc tcatgctgta gcagaccagg    2580
agcaggagca ttggtgactc ctttaggag  tttaccacgg ggcccgggct cggtggctca    2640
cgcatgtaat cccagcactt tgggaggccg aggctggtgg atcacttgag gtcaggagtt    2700
tgagaccagc ctgaccaaca tggtaaaacc ctgtctctac taaaaacaca gaaaatttag    2760
ctgggcgtgg tggtgcttgc ctgtaacccc agctactcag gagtctgagg caggggaatc    2820
acttgaaccc cggaggcaga ggttgcagtg agctaagatc atgcccccac actccagcct    2880
gggtgacaga gagactcaaa aaaaaagttt accacgcaga ctggatcaaa aaagcctgtc    2940
ttcttttggt tttccttcca tctaactgta tccctccttg gttctagaag cacacatctg    3000
accacttgtc tttcctcttt ctctgtcatt cctgttttcc acactccttc acagctgctt    3060
cctttgcaaa tagccaaaag tgaagtcatt ccagaactcc taaaagtttc ttcttaaatg    3120
tcatatgatt aaagacattt cagacttttg cacaagttca gtgttcatca attattcaca    3180
tttttttttt tttttttag  agacacagtc tcactctgtc atccagcctg gagtgcagtg    3240
gcatgagatc atgacccact gcagccttga cctcctgggc tcaagtgatt cccccgctgc    3300
gctgtcagcc tctcaagtag ctgggaccca taggcgtgta attttaaaa  tttttgtag    3360 agacagggtc ttgccatgtt gtccaggctg gtccccaact cctgggctca acaatcctc     3420 ccgcctcggc ctcccagagt gttgggatga cacccccgc  acagctccaa ttttaaaat    3480 taaataaaat aacacactca ccatcattgt aagaatcaca tgaaatatac caaagtgctt    3540
tgtaaactaa caaaaaattt atttcttgaa ataaatgtgg ccaggtgcag tggctcacaa    3600
ctgtaatccc agcactttgg gaggccgagg tgggcagatc acttgaggtc aggagtttga    3660
gaccagtttg gccaacatgg tgaaacccg  tctctaataa aaatacaaaa attagttggg    3720
catgatggtg cacgcctgta gtcccagcta ctcgggagac tgaggtacga gaattgcttg    3780
aacctgggag acagaggttg cagtgagccg agatggtgcc actacacgcc agcctggatg    3840
acagagcaag actctgtctc aaaacaaaaa caaaacaaa  acaagaaaaa taacgtgat    3900 tttttttttt ttttgagac  aagagtctcg ctctgtcacc caggctggag tgtagtggtg    3960
```

```
cgatctcagc tcacttcagc ctccgcctcc caggttcaag caattcccct gcttcagcct    4020
cccgagtaat tgggactaca ggtgcaagcc accatgccca gctaattttt gtattttag     4080 tagagaccgg gtttcaccat gttggccagg atggtctcga tctcttgacc tcgtgatctg    4140
cccaccttgg cctcccaaag tgctgggatt acaggcacgc accaccgcgc ctggccagaa    4200
acgcgatttt aatatctaaa ttgaaacctt aaaaacactg atgtatttag gccaggtgct    4260
gtggctcaca cctgtaatcc cagcactgtg ggaggccgag gtgggcagat cacttgaggt    4320
caggagtttg agactagcct ggccaacatg gtgaaagctc atctctacta aaaatacaaa    4380
aattagccag gcatgatggc aggtgcctgc aatcccagct actctagagg ctgaggtggg    4440
agaattgctt gaacctggga ggcggaggtt gcaatgagct gagattgcac cattgcactc    4500
cagcctgggc aacagagcga gactctgtct caaaaaaaaa aaaaaagaa aagaaaagaa     4560 attactagaa gaaaacactg ggggggggg ggccaggcac ggtggctcac acctgtaatc     4620
ccagcacttt gggaggctga ggcaagtgga tcacctgagg ttaggagttc gagaccagcc    4680
tgggaaacat ggtgaatccc tgtctggact aaaatacaaa aattagacag gcatgatgga    4740
gggtgcctgt aatcccagat actcgggagg ctgagacaga gaatcgcttg aacccaggag    4800
acagtggttg cagtgagcca agattgcgcc actgcactcc agcctaggcg gctgagcgag    4860
actccatctc aaaaaaaaaa aaaaagaaa agaaagaaa gaaaacactg gggaaatgtt       4920
ccagggtatt gatctgggca agacctcaa agcacagaca acaaaagcaa aaacagacaa     4980
atggaattac atcaaactaa aaagtatatg cacagcaaag gaaacaacaa agcaaagaga    5040
caacacacag aatgggagaa atatttgca aactatccat ttgatgaggg actaatgact     5100
agaatatatt aggagctcaa tagcaagaaa acaatcagat ttaaaagtgg gcaaaagatc    5160
tgaatagaca tttctgaaga gatacaaatg gccaagagat atgaaaaagg gctcaatgtc    5220
actaatcaga gaaatgcaaa taaagacagt aagatatcat ctcatcccag ttaaaatggc    5280
ctttatcaaa aagggaataa catgctgaga tggatgtgaa gaaggaacct catacactgt    5340
tggcgagcat ctcaattagt gcagccacta tggaaaacaa tatggaatcc tcagaagatt    5400
aacttctgag aaatcataag ttctggaatc ataactacca tatgatccag caatcccact    5460
accggtatat accaaaaaga aggaagggc caggcacggt agctcacgcc tataatccca    5520
gcactttggg aggccgaggc aggcagatca cttggggtca ggagttcaag accagcctgg    5580
ccaacatagt aaaaccctgt ctctactaaa aatacaaaaa ttagccaggc atggtggcac    5640
acacctgtag tctcagctac tcgaaagact gaggcacaga aattgtttca acacagaggc    5700
agaggttgca gtgagccaag atggtgccac tgcacttcag gctaggcgac agagcaagat    5760
ggagtctcaa aaaaaaaaa aagaaagaa aatcaatata tcaaagagat atttgcactc     5820
ctatgcttat tgtagcactg ttcacaacag tcaaatatg gaatcaacca aatgttcat     5880 caatggatga ctggataaat aaaatgtaaa tatacacaat gaatactatt cagccataaa    5940
aaataataaa atcctatttg caacaacatt gatggaactg gaggtcatta tgttaagtga    6000
aacaagccag gcaaagaaag acaagcatca catgatttca ctcataaatg ggaagttgaa    6060
aagtggatat catgaagata agttggtggt taccagaggc caggaaggt agccaggaga    6120 aggggatgaa cagggtgatt aataggtaca aaaattggta gaagtgctgg gcaaggtgtc    6180
aagagcccca gcatcagaaa gtggtcgact tgctggttgg taagaagaat ttatcgacaa    6240
caatataggt ttgaaaaagg aaagttttat tagaacgctg cagaagagtg cagcctcagc    6300
```

```
aagagagaac tgagcatgcc gcggtggatt tttcatgtcc cttttcgaat gtctcatttt    6360
ttgcaaattc aatccaagtt gcgttcattt agccaggatc cttctaagct cattcaagaa    6420
ttttgggctt taactatttc ctttgattta acctggtacc aggtgccaac tttagataat    6480
agggatatct aattacttct aaattcctca gataagggc ctgcttgatg gtcaccaggt    6540
gatctgtgct ctccttaaga gggaataaga cctagcgttg cagagttct gtagggtgac    6600 tatagttaac agtaatctgt tgtatatttt aaaatgttat tattgaagag agtaactgga    6660
atgttcccag tataaagaca aatgtttaag gtgatagaga tctcatttac cctgatttaa    6720
tcattacaca ttatatgaaa gtatcaaaat accacatgta cccagaaaac acatacgtct    6780
cttacatatc aataaataca acttgagatt atgatgtaaa tacatctgac caacttggta    6840
cttattagac ttatgtgcgc agcactgctc tagtcctgtg ggtgcagcag catcaggatc    6900
gttaaagaaa acaaacaatg ctgagaaaaa aactcacacc cctgagacat ccgggtgtga    6960
ataaatgcgg cagagtcgcc cgagatcggg agaccaggcg tgggggagag gtccgggagg    7020
cctggaccag agtcctaaca gaccagaggc gaaacgggaa ggcgcgccag aaaaggaaca    7080
acgcaaaggg agcaggcgtg cacggagcgc gaactaagga cccctctga caaccccagt    7140 ccctcggcag ttccagagac cggctcctca cggagggtgg cggtagagac tgttaagccc    7200
cgcgggcgcc ggggcaggcc ggactgtgcc attcgtgggg ggtaccatgt gggaccgagc    7260
cgcctcaccc agggctgtcc agctagaaac tccccggtgc cacccccgcc tcagtccgag    7320
gtagactcgg ccggacgtga cgcagcgtga ggccaaggcg gcgtgagtct gcgcagtgtg    7380
gggctgaggg aggccggacg gcgcgcgtgc gtgctggcgt gcgttcattt tcagcctggt    7440
gtggggtgag tggtacccaa cgggccgggg cgccgcgtcc gcaggaagag gcgcggggtg    7500
caggtcagcc ccagcggggg cgcggcgcat gtgtgggccg tggcgctggg cggcgtgggg    7560
gtgctggacg gtgtccctgt gctggacggt gtcccgctgg ctcagaaccg gcgcggggcc    7620
tgggtcgggg ccgccctcgc ttccggcctc ccagtcgggc cctgtcgctg gcgttggatt    7680
tgactgaccg ccagcgtggt ggcaacgctg aagcgtccag aatcttctgc ctaacctctc    7740
gccggcatgg aactggctag ccgttttatt aaactctgtt ttgcgtggac ggtaaaccct    7800
ccagataatc tgtaaatagg ctaaaaaaaa ttcggaacct cgttgagctg ctgtcgttgg    7860
cagtgagaac tccgcgcaga gagacagatg tagttgggtt gacttcagtg aggggatttc    7920
catctttctc agtcattaaa aaaagtgttc agacatttaa cactgttgac ccccacacac    7980
aattttttag tacagttata actaagaaaa caaaaatccc ctccaaaaaa ttacaagtta    8040
attgcgaaag accacatttta aatttttgcc catgaaattc agtttagtcg tttctctgaa    8100
acagtgcttc aaaaaagact gtttccccgc attgtgtgaa atgcaggaga cccacgtact    8160 tgtatttta aaaaacccat ttgcaacata ctattaaagt tggatttaag agaacatggt    8220
agaagaaaat ctaagcaata ctacaccttt tagcaccctc attatgtttt catctcagag    8280
caattaaaac tgctatacaa atcaacgtta agataactaa actgctgctt ttttcgtatt    8340
cagttgtcta tgaaaaccgt ttccctagga agtacttact ctgcttgaaa atgctcctaa    8400
actttaaatt tggggtatc tcaggttgc aatgaaagtt ttttgaaatc ttttttttt    8460 ttttttttta aggcttgtaa acatataaca taaaaatggc ttccaaaaga gctctggtca    8520
tcctggctaa aggagcagag gaaatggaga cggtcatccc tgtagatgtc atgaggcgag    8580
ctggggtaag tccacatcg attttagcc attcctgttt taaatgtttt tggattttta    8640
aatcattttg aataaaatat tcaaagtgct ctatgaaata tttcaaatat acacaaaatt    8700
```

```
tcagagatga cataagaata aatacctgtt gatccactgc tcacatttaa cgcttgttaa    8760
tgtcttgcca tatttccttc agacccattt ctcttttgtt ttgagctctg tcgtccaggc    8820
tggagtgcga tggcaggatc ttggctcatt tcggtctctg cctcctgggc ccaaaccatc    8880
ttcccacctc agcctcccaa atagctgaga ctacagatgc gtgccaccac acctggctaa    8940
tttttgtatg ttttgtagag acagggtttt gccatgttgc ccaggctgct ctccaactcc    9000
tgagctcaag ttgtccaccc gcctcaggcc tcccaaagtg ttaggactac aggcgtgagc    9060
cactgcactg tccttagacc catttctttt ttcttctttt ttttttttt tgagatggtg     9120 tctctctgtg tcgctcagcc tggaacgcag tggtgtgatc tctgctcgct gcaacctctg    9180
cctcccgggt tcaagagatt ctcctgcctc accctcagct gggattacag gtgtccgcca    9240
ccacgcccgg ctaattgtat ttttagtaca gatggggttt caccatgttg gccaggttgg    9300
tctcgaactc ctggcttcaa gtgacccgcc cgccttagcc ttttacagtg ctgggattac    9360
aggcaggagc caccatgccc ggcccctcag actcgtttct taaagagcag atgcttcaaa    9420
gaaatacatt tgaagccccc tttgtaaatt tctccaatcc tatgcccctt cttccttcct    9480
taaagataag tgctatcctc gcactcttgt gtatccatgc atgtgtgtct tttttttttt    9540
ttttaagaca gagtcttgct ctgtcaccca ggctggagtg cagtggtgtg acctcagctc    9600
actgcaactt ctgcctcctg ggttcaagca gttctctgcc tcagcctccc aagtagctgg    9660
gattacaggt gcgcaccacc atgcctggct aattttttgt attttagta gatgggtt      9720 caccatcttg gccaggctgg tcttgaactc ttgacctcgt gatccaccca cctcggcctc    9780
ccaaagtgct gtgattacag atgtgagcta ctgcacccgc ccccacgcat gtctttaagg    9840
tagcatttga ccgtggttct cattttgcgt gtttatatat tatctctctc tatctaaaaa    9900
tagtgaacag tgaagtgaag tagaactaac tctgtgccag gcagcattct aagtgccgat    9960
aaaccttaca acaatgtcgt gagttagata tcaccatcct cattttacag ttgaagaaac   10020
tgaggcacag agacataaat aatgtaccca catcacgtag taagtacaaa agccagaact   10080
cagacccagg cagcctggcc ccagagtctg ttaaccctat actcctctgg ttctcagaaa   10140
tgaagataca tgtcgattaa gtttatccac ttaaaattgc tgcttggtgt tgcactgaat   10200
gccacaatct acccattcct ctaattacag cattacaatt ctgtaatacg tattcttgtg   10260 taggttttctt tgtgcaaatg tgaggaaatt tttccaggtt atatatctaa aagtagaatg   10320
actaggccga aggatagcct gtagtcagca tgactaggtt ttgccaagtt gctctccagt   10380
gtcccagttt gtagtcccac cagcagtgta ggaaaattcc cactttccca gtgccagctc   10440
ttggtattgt tgactttaaa aattttgaa agataaagca gtatttcgtt gtttggactt    10500
gcatttctat tttacaaaaa taccatgagg tttaaatggc aacagtaaac ttgcaagatg   10560
agttattaat aggatgatca tataactggt cacccaaacc agaacatttg tgggagaaag   10620
ggtgttccag tccacagag tacagggcag cagctataag tagggtctgt cccgggcaaa    10680
ccagggtaga cctagttatt aaatatattt agccagtgta ttagcttaaa tttggtatag   10740
ttgtggtgca gtatttcctg tcatgttact ttcaaacaca gggcagctgt gtaaacgtta   10800
ctctagctgg gtgtggtggc tcatgtcgt aatcccagct acttgggagg ctgaagcagg    10860
aggatcattt gagcccagga gctggaggct gcagtaagct atgattgtgt cactgccctc   10920
tagcccaggt gacagggtga gaccccatct ctcttttttc tttttttta aagacagtgt    10980 tactctgaat ttatgtttca gtgttcttaa atatgataac atctttctcg tagattaagg   11040
```

```
tcaccgttgc aggcctggct ggaaaagacc cagtacagtg tagccgtgat gtggtcattt    11100
gtcctgatgc cagccttgaa gatgcaaaaa aagaggtttg taatccatac atggagttat    11160
tccttcatat ggcttctttg tttcttgaaa tgtcttaaga gtgttgttag cacagactca    11220
ttttagaaaa ttattttgct tgaatgtctt cccctgacag attaagaggg tgaggacttt    11280
gtctttctat tctgtatctg tagaatgtgg caattgcttg atacagaatg tgcttagtaa    11340
gtgggtggct ggatgggtag gtggccggtt ggatgtgtgg ccagatgggt gggttggtgc    11400
ttagatggat ggctgcattg ttttcccatc agtattttc tggcttacac aggcatcctt    11460
gcctcctatt acacattttt acctgacata aatcaactgc cacatttttcc attttttatt    11520 attattattt ttgtttagag gaatggtccc actctctccc ctaggctgga gtccagtggt    11580
gcagtcacag ctcactgcag cctcaacctc ccaggttcaa gcaatcctcc cacctcaacc    11640
ccccacgtag ctcggactac aggcatgtgc catgcccggc cattatttt tctaaagata    11700 ctttcagagt tccactgtag ttgtgttgtt ttttcagtat cgttggaatt atggctctta    11760
cctttaagga cgatggacac ttttggaagc tagcatccct ttcctcagaa acatgctccc    11820
ccacaggcgc ttttgcacac tccgtcgtgc ggtcagcgtg acaggagtgt ggactgtacc    11880
ctctgacagc agggtcatgg caggaaagga ggcagagtcg gctcacagat ggctggttgc    11940
acactgctga ggaacctgga gtgcggttcc ctgggccgag ctgtcctcag atacatagga    12000
aaaagtttaa tccttctcaa taagtttaga ttttcatta ctggattgta gaaaattaga    12060
ctgttggtat ttacatgtga tttgttgaaa caaattaaaa atgacaagca gaagtaagta    12120
ttccaggcca agtgcagtgg ctcacctgta atcccagcac ttttggaggc caaagtggga    12180
ggatcacttg ggaccaggag tttgagacca gcctgggcaa catagcgaga ccgtttctct    12240
ttaaattaaa aatttgtaaa agccaggtgt ggtggtgcat gcctgtagtt ctagctactt    12300
aagaggctga ggcaagagga tcacttgagc ctagacggtt gcttgagccc aggaatttga    12360
gacagcagtg aactgtgatt gtgccattgc ccttcagcct gggtgacaga gcgagaccct    12420
gtctcaaaaa taataataat acttttttc atctctgttt gtgttttgt catatgatgt    12480 ctgggcattt taaaacagtg gttaccttta ttttcaatcg acagataata agtgtacata    12540
ttcatgggat ttgtgatgtt tccatgcata atatatagtg atcggatcag agtaattagc    12600
atatccatca tctcaaacat ttcttttgtgt tgggaacgtt caatatcctc cttgctatttt    12660 gaaactatat atgattgtta actatagtca ttctacgggg gtatagaaca ccagaaccta    12720
ttcctcctat ctagctataa ttttgtatct tttaacaaat ctctccctat ccccactttc    12780
tcctatcctc cccagcctct agtatcctct gtcctacatt atgcttctat gtgatcaatt    12840 ttttttttagc tttcacatat gagtgagaac atggagtgtt taatttgcta ttcctggctt    12900
ctttcactta atataatgtt ctctagttcc attcttgtag ccacaaatga caagatttca    12960 ttcttttta tggctggata gtatcccatt gtgtataaat gccacatttt ctttatgcat    13020
tcatctgttg ttggacctag gttgatttcg tatgttggct agtgtgactg ttggtgtagt    13080
aaacaaggga gtgcaggtgt ctcttcagta tactgatttc ctttccattg gatacatgcc    13140
aagtagtggg attgctggac catatggtag ttccatttac tgtagttttt taaggaagtg    13200 gttaccttt gtgtgttttt atttttcagt gcagattcta aaaggagtaa aataaattct    13260
atactttaca catttctttt tgagttttga gctttgcttg gttttgaatc aacggtagga    13320
tgtttatggt cttaaaagtg attctaagcc agccatagtg gttcacacct gaaatcctag    13380
cactttgtga ggctgaggca ggaggattac ctgagcccag gagttttgag actagcctgg    13440
```

```
gcaatgaagc gagaccctgt ctctacaaaa ataaaaaaaa ttagctggct gtggtggtgc   13500
atgcctgtag tcctagctcc tgcagaggct gaagtgggag agttgcttga gcccaggagt   13560
tcaaggctgt agtgagccac gattgcatca ctgcactcta gcctgggtga cagaggtgag   13620
ggcttctctc taaaaaaatt ttataggttg cactaaatac ataatacatt tttattttgt   13680
aatttgttta atgactagat ttttttaac cacttttta agtactaaag tattgttggc      13740
cggccacagt ggttcacgcc tgtaatccca gcactttggg aggccagat gggtgtatca      13800 cgaggtcagg agtttgagac cagcctggtc aagagggtga acccccatct ttactaaaaa   13860
tacacagatt agccgggcac agtggtgggt acctgtaatc ccagttgctt gggaggctga   13920
ggcaggagaa tcgcttgaat ccgggagacg gaagttgcag tgagctgaga tcactgcact   13980
ctaacctggg tgacagagca agactctgtc tcaaaaaaaa aaaaaaaga aaagaaaaat     14040 aaataaataa ataaaaagtc ctaaagtatt gttaaaacaa tttccgtttt gtaatttcag   14100
gaagtttgaa attaatttga tttctaggat tttttggggg ggatactaaa attctccccc    14160
cgttacattt ttcataaagt taagaaaaat ttttttgtgcc ttttacttaa aatttgtttc  14220
tctattaatt ttatttgttt ttttagacag agtcttgctc tgttgcccag gctagagtgc   14280
ggtggtgcag cctcagctca ctgcagcctc tgcctcctag gttcaagcga ttctcctgcc   14340
tcaacccccc aagtagatgg gaccacaggt gtgcaccacc acaccagct aattttcata      14400 ttttttagtag aaatgggggt tttgccatgt tggccaggct ggtctcgaac tcctgagctc   14460
aggtaatctt cctgccttgg cctcccaaag tgctgggatt acagacatga gccagtgtgc    14520
ccagcctgtt tttctattaa ttttttaagt tgttcatgta cattcttgtt gaacaataat    14580
tcaaacaata tagacacata taagtcaaa atgttaaatg tcctgttctc attctccctc      14640
tgccccatcc cacactactc ccattagcaa ctagagtgtc ttcctttgtc tgtgactacc   14700
tgtatacaga atatgtgggg tggggtgctt gtggtgattg tacacataca cgcatacatc    14760
tacacacaaa tacatatatc cttgtctttt acaggaagga gattatacta cccctgctac   14820
tctgcagcgt ggacatcctt gcatgtcact acatacaggt tttctgcatt ttttgctagt   14880
taaaacacca ttccgtcatg tggatacacc ttaatttatt taactgttct attggcagat   14940
aggctatctc ctgtacttcc cacatttaaa ataggaaagt attattggac tgtcaatta     15000 atgcacagtt gaaatgaaat gttttgtttt tctttatgtt ttaaactgtt acagggacca   15060
tatgatgtgg tggttctacc aggaggtaat ctgggcgcac agaatttatc tgaggtaaaa   15120
aattctactc aattataccct caataaagct ggggggggg aaaaactaaa gaatttcagc   15180
atctgcttat gttctgttaa ttttgttatt attcaaatat ttcgggagga ggctgtgaaa   15240
aaaaaataga aacaactaaa attaacaaaa tggtgttata gcattaactc aaactttttt    15300
ttttttttga cagagtctt tgctctgtgg cccaggctgg agtgcagtgg cacaatctcg     15360
gctcactgca atctccgcct cctgggttca agcagttctc ctgcctcagc ctctgagtag   15420
ctgggattgc aggcatgcac ccccatgccc tgctaatttt tatattttta ttagagacgg   15480
ggtttcacca tgttggccag tctggtctca aactcctgac ctcgtgatcc gcccacctcg   15540
gcctcccaaa gtgctggaat tataggcgtg agccaccact cccgacctca agaaaacatt   15600
tttaatattt tctatggagg tcaggtgcag tggctcaacg tctataatcc cagtggtttg   15660
ggaggctgag acaggaggat tgcttgaggc caggagtttg agaccagcct aagtaacaca   15720
tcgagacgcc atctctacaa aaaatttct tttaattagc tgggcacggt ggtgcacact    15780
```

```
tgtagtccca gctactcggg aggctatggt gggaggatga cttgaggcca gggatttgag   15840
gctgcagtga gctgtgaatg caccactgca ttctagcctg ggcaacaaag caagaacctg   15900
tcttatcaga aaaaaaaaat gttgccatgg aagtaagctg aattggtggg accgttatga   15960
acagatgtcg atgaatacag tccaaagtaa gatgatttgg ttttttttcca ccagcagaag   16020 aatgatcaga ttttgtgttt tgagaagggc aaattgtcta ctcaaagtct taactggggg   16080
aagctgtggg gctagggctg ccagcaggaa tggcaaatgc catcagcaga gaccattgtt   16140
cctcatttta agtcgtatgt gaggagtcag aggccagggt gaggggcaca cctgcaggca   16200
gagttggggc tgccagaagt aagaagtggg ttgtgtcaga cacaagggat cttttcctgc   16260
tagattctgt tcctctctct gccatctgaa acacccaaa acaccacatt ccctcccatt     16320
tctttctccc tggagtacaa aatggcaagg gtcaaattgc ttcttctgat ctttaaatgt   16380
ggaagagtgc gtttctctta tgagaaatgc cttgcttggg tttaagaata taatatagac   16440
acattttgat cattttata ccaatgattt agaaatattg ttggaaaata ggtcagagag     16500
cttgtggttt aaactaaaat taaattcttc caaagtttcc tagtgagtga ttggttagtg   16560
gcttaatgat aacttatgt attttggtt ttcttttcac tagtctgctg ctgtgaagga      16620
gatactgaag gagcaggaaa accggaaggg cctgatagcc gccatctgtg caggtgacgt   16680 gcagggcag cctgtgttgc agcgtcattg gtgggtgggg tagccttttca ttcgatggtt    16740 tgattccaaa tagctcttcc ccttcataaa gcatgcaggg catctgtgtt ggtgtattta   16800
gtttgggtgg catgaagttg gtgtcatttc agagatgagg acaattgttc tgttttctgc   16860
ctctccatgc ctttggtcta catgctgtga aacttagtgt tttccgtgtt tggttgacct   16920
cggaggaaaa taaggccctc tggaattcag taaacagctt gttacagcaa gtctctgtgc   16980
cagaaagtct ttgtgccagc acacaatcag caaaatccat caaacatcaa cacagcagct   17040
ctgtcctgtg cttgccctgc aaattcagaa gccccatgg tgctttccgc tggcttctcg     17100
ggcgtttctg attgtctcag taccgagtga tcttgggcac cgcattatct gccacataat   17160
ttagaacaag gacatttggt gcttcgcaga tgtcctcttc tctttgtacc ttagtaatat   17220 tttatttct cataaccatt ttaagatcca ttcttgttgc tttcctatca gatgatgttc     17280
tgccattttg gttttttccc atgctgtaat ttttgccagc accttccttg ttgtataggt   17340
cttcattaaa tatttgtcag ggccgggcgc agtggctcac gcctgtaatc ccagcacttt   17400
gggaggctga ggcgggcaga tcacctgagg tcaggagttc aagaccagcc tggccaccat   17460
ggtgaaaccc catctctact aaaaatacag aaattagcca ggcgtggtgg cgggcgcctg   17520
taatcccagc tactcgggag gctgaggcag gagaatcgct tgaacccggg aggcggaggt   17580
tgcagtgagc cgagattgtg ccgttgcact ccagcctggg ggacacgagc gagacttcgt   17640
ctcaaaaaaa aaataaaata aaataaaata aatatttgtc agaagagtga atgaataaac   17700
gaatgaatga gtggatggtt tggtaaacat caacatcaaa acatgttgct gttgctatt      17760 tgttcaatac agtaggcttt tcaaaagaag ttatgggcca gaggtcctgg ggacttgata   17820
cattcgagta tcagtggttc tcaatgttct tttggtgcac ttgcaaggtc aaagcagatg   17880
ctactgaggg gccaggtgtg gtggctcatg cctgtaatct cagcattttg ggaggccaag   17940
gcagaaggat ctcttgaaag ccaggagttt gagactaacc ttgcaacat agccagaccc    18000 ccatctcaac aaacaaacaa acaaaaaatt agccaagcac agtactgcat gcatgtagtc   18060
ccagctactc aggaggctga gatggggagga tcgcttgaag gcaagagtta gaggctgcag   18120
tgagctatga ttgcactcca gcctgggcag cagagtgaca ccatgtcttt caaacaaaat   18180
```

```
gttattcgcc ttttttcttc tcagtctttc aggagtgaca tcagagtagg atgataccat    18240
catctgagaa tttattattg tgttttaaaa atttcccagt tttattaggt tgatgtaaaa    18300
gtaattgtgg tttttgccat taaaagtaat tggcgtggca cagtggcgca tgcctgtaat    18360
ctcagcactt tgggaagctg aggtgggcag atcgtttgag gtcaggagtt caaaaccagc    18420
ctggcaaacg tggtgaaatc ccgtttctac taaaaataca aaagttagct gggcatggtg    18480
gtgcacgcct gtaatcccag ctactcggga ggctgaggtg ggaggatcac ttgaggtcag    18540
gagttcgaaa ccagcctggc taacatggtg aaaccccgtc tctactaaaa atacaaaagt    18600
tagctgggca gttagctggg tatggtgatg cattcctgta atcccagcta tcaggaggct    18660
gaggcaggag aatctattga acccgggcgg cggaggttgc agtgagccgc gattacgcca    18720
ctgcactcca gcctgggtga cacagcaaga ctgtctcaaa aaaagtaat aatttttaat     18780 atggcagatg ttcatagata taacccacat aaaagctaaa gggattctaa gacctaaatg    18840
tttgagaacc gtggcattag gggctgggaa gaaccacaga ggttgaccac cctggcaggt    18900
cttgtacgtg ggcttactac aagagtcacc actagccttt tgacctgccc tgaggctcag    18960
gtaattatct ctgccaaagg gcactgcagt cactgcagcc caagcagctg ctcccctctt    19020
tggagagaaa gtcacagatc cttgagtttg gttttctttg gctctgctgc tgtgaagcaa    19080
gcctcagtcc tagattcttt gaccaaagga agaaagagtt tgggctgagt ttgtttcctt    19140
atgattctgc tgaaagtaaa aaccacatgt cagtttgtcc tgtgccacaa aagtagcaaa    19200
atcacttaag gtcaggagtt cgaaaccagc ctggccacca tggtgaaacc ccatctctac    19260
taaaaataca gaaattagcc aggcgtggtg gcgcgtgcct gtaatcccag ctgcttggga    19320
ggctgaggca ggagaatcgc ttgaacctgg gaagtggagg ttgcagtgag ccaagattgc    19380
gccattgcac tccagcctgg gcaacaagag tgaaactccg tctcaaaaaa taaataaaat    19440
aaaataataa aaataaaaat aacaaaaatt agcagggcat ggtggcgcat gcctgtcgtc    19500
ctagctactt gggaggctga ggcaggagaa tcgcttgaac ccgggaggcg gagattgcag    19560
tgagccgaga tcgtgccact gcactccagc ctgagcgaca gagcaagact tcgtttcaaa    19620
aaaaaaaaaa aaaaatcaac cacatttggc ttactgtttt gtgctgaggc tagatggaat    19680
gccatgctaa gaagcatggg ccttatagta ctttaaatca acattaaaaa ataaacaggc    19740
tggctgtggt ggctcatagc tgtaatccta gcactttggg agactgaggt gggaggatca    19800
cttgaaccca ggagttcaag accagcctgg gcaacatagt gagacccccc caccgacctc    19860
tacaaaaaaa tattttaaaa aatcagcctg gtgtggtggt gcacacttgt agtcccagct    19920
actcaggagg ctgaggtggg aggatcactt tgagcccagg aatttgaggt tacattgaga    19980
tgtggtgatc acaccactgc acttgagcct aaaggacaga gcaagacttg gtctcttaaa    20040 aaaaaaagt aaaaataggc caaggggcggt ggctcacacc tgtaatccca gcactttggg   20100
aggccgaggc gtgcggatca caaggtcagg agatcgagac catcctggct aacacggtga    20160
aaccctgtct ctcctaaaaa tacaaaaaat tagccaggcg tggtggcggg tgcctgtagt    20220
cccagctact cggaggctg aggcaggaga atggtgtgaa cctgggggc agagcttgca     20280 gtgagccgag attcgccac tgctctccag cctgggcgac agagtgagac tccatctcaa    20340 aaaaaaaaa attatataaa aaacagtaaa aatagaaaac acactagcag tgtgtttata    20400
ccattgaata tcctgcacca ctgttgtggg cactacacca gaaataggaa aaaatgtgat    20460
gatgagctga gctaattgag atgagggtta tgggaatgga acagaggagt gatggaagag    20520
```

-continued

```
atttggatct tttaaattgg caaacagaaa aataagattc tttttttttt ttttttttgt   20580
tgaaatggga gctttgctct tgttgcccaa gctggagtgc agtggtgcaa tttcggctca   20640
ctgcaacctc cacctcccag gttcaagcga ttctcctgcc tcaggctccc gagtagctag   20700
aattacaggc acctgccacc atgcccagct aattttgta tttttggtag agacggggtt    20760
tcaccatgtt agccaggctg gtctcgaact cctgatctcg tgatccgccc accttggcct   20820
cccaaagtgc taggattaca ggcgtgagcc accgcaccca gccaagatta ttctgaagtg   20880
ttgcagttag ggattggaaa cattttgaac acaaagaata ttagcctagt ccttaatatt   20940
gagtgaatga ggaacgcaaa ttggaaggga gtctatgttg agaagaaaat taaatgatat   21000
ttactttgag taggggaggg ggaggaagtg tggagttgga ggagtggaca gttgtcagct   21060
gagatgccca ggtctaggaa tgaggcctct ggaagcaagg tcttggccac ctggaggagc   21120
tggggagttg gcagaggtgg tcattttgca tgttaccaca gggtggtgct gttggctgca   21180
gaagggggaca tggtcagctg cgccctctgc actgtagtgc agagtacaga gcgttttcat  21240
ccatcagaat cccaggtcct gggagagtga aacgtctctt ctccagtatt ccaaataggg   21300
ttctgacgcc ccagaaagca gtgattatga gcttacctga taagtatgaa agacatcagt   21360
aaattcctga atccaactgt aacataaatt tattcacatc gtagcagtga ttttattacc   21420
accttgaagg gagcagccta aaaattctcg ttccgatc actttcctca ctgtgctatc     21480
atctattaaa gtttactta aaatgcaaga tgatgtagga atttcttctt aaattcttac    21540
caaataaaaa ttaaaaacaa tttataaatc cattcaaata aaaattgata attattcaat   21600
tcttacggac ttctaaaatt tgctaccata catagctgtc ttgtgtgtaa aaataacgtg   21660
gagaagagac atttgaggct tttgatttaa gagctataaa tcaggacttg gtctgaaact   21720
gacagctgat attaggcaga aagcttatgt aattaggtag tatttgtgtg atcttcctgt   21780
ttgtaacagc tacggtctga gtagcttgtg ggtatattat ataattcctt ccttggagtc   21840
ttgttgaaaa atgaaaggac agtaagacca agacctctca ggtttgctga cactaaaagt   21900
gtacaaactg tgccacagga tcttagccat ccagggcacc ttaagtgttt ccaagatcaa   21960
ggtgctgttc tgaaacgtat ccttctaagt gtcatgtgag gccttagaaa gaatgtttat   22020
atgtgtggct tagaggaaaa aggtagaatg aatactttgt aaaaagcttt aagatgaaat   22080
aacaatgaaa ggtatataaa atcttttgttt ttaatcctta tttaggacca ttacatacgc   22140
aatatgcttg tgaccctccc tgaagttggc cgttttcagt gaatacattt aaataaaaat   22200
ctcaagttag gacctgccaa tttggaaaga cttcatcaac tgacacttcc atgtggttct   22260
ttgcttaagt agctttcatc acgtgatgct agtgccttta tatctcacac ttccaggcac   22320
ttcacaggct atctccttca aggacagtgt gctgtccatt ttaatcctac cacctggcat   22380
acttgggtgg ataggtggat gaacgagtgt taatttccca ttttatttat ttattttta    22440
tttattttga cacagagtct cgctctgtcg cccaggctgg agtgcagtgg cacgatcttg   22500
gctcactgaa agctctgcct cccgggttca ccccattctc ctgcctcagc ctcccgagta   22560
gctgggacta caggcgcccg ccaccacgca cagctaattt tttgtatttt tagtagagac   22620
agggttccag cgtgttagcc aggatggtct tgatctcctg acctcatgat ccagccgcct   22680
tggcctccca aagtgctggg aatacaggca tgagccaccg tgcccggcct aatttcccat   22740
tttcaagtag aaaataagat tacaaaagag caataaaatc cagaagttca gagagtacca   22800
gttgccttta gcatgtaact aaatctttcc ttttactaag agtgaggtaa gaagttgagc   22860
ccgccccagt gatcctcccc ctcctttgga ctcctggtat atgtggtccc tgttctgggg   22920
```

```
atgggaagg tgagagaggt gagcacattt tgtttatctg tgtatgctct gctggtatca    22980
aggtaaatct tcttgagtaa atggttattg aagtattttg agtttctgtg cttttgccag    23040
atgtgctcag caaatcgttt gttataaaca tactttatct ctcatactag gaagtgtttc    23100
atttcagaat cgtagctgta tgtttggtaa gagcctcttg attttgaaga atactttgct    23160
gttgcagttt tgttgttgt tagagaaggg gtctgtgttg cccaggctga tgttgaattc     23220
ctgggctcaa gcaattttc tacctaggcc tccccaattg ctgggattac aggcatgagc     23280
cactgtgcca ggcactattg cgatttttta aacatgggct tttctatatc tgcacttaga    23340
tcttttatt tttattctta ggtcctactg ctctgttggc tcatgaaata ggttttggaa     23400
gtaaagttac aacacaccct cttgctaaag acaaaatgat gaatggaggt aagtatatgc    23460
ttgttttgt ttgtttgttt gtttttgag atggagtctc gctccatcgc ccaggctgga     23520
gtgcagtggc gtgatcttgg cttactgcaa tccctgcctc ccgggttcaa gcgattcttc    23580
tctctcagcc tcctgagtag ctgggattac aggcgcatgc catcacaccc agctaatttt    23640
tgtatttta gtagagatgg agtttcacca tgttggtcag gctggtctca aactcttttt     23700
ttttttttt tttttttttt ttttgagaca gagtctcgct ctgttgccca ggctggagtg     23760
ccatggtgcg ttctctgctc actgcaactt ccgcctcccg ggttcaagtg attcttctgc    23820
ctcagcctcc tgagtagctg ggatcacagg tgtgctccac cacgcctggc taattttgt    23880
attttttagt agagatgggg tttctccatg ttggtcatgc tggtcttgaa cttctgacct    23940
tgtgatccac ccgcctcagc ctctgaaagt gctgggatta caggcatgag ccaccgcgcc    24000
cagtctcgaa ctcttgacct tgtgatctgc ctgcctcagc ctcccagagt gctgggatta    24060
caggtgttag ccaccgcgcc tggcccatat gcctgtgtgt ggttttttt ttttttttga    24120
gatggagtct ctcgctctgt tgcccaggct ggaatgcagt ggtgtgatct cagctcactg    24180
caacctccgc ctcccgggtt caagggactc tcctgtctca gcctcccgag tagctgggat    24240
tacaggcatg tgccaccaca gtttcttgt agactgggca cagtggcttc cgcctgtaat    24300
cccagtactt tgggaggctg aggcgggtgg atcgcttgag ccccgagttc gagaccagcc    24360
tgggcaacat ggttaaactc catctctact aaaaatacaa aaacattag ccaggcatgg     24420
tgatgcacac tggtagttgc agctgctcag gaggctgagg tgggatgatc gctttaagcc    24480
tgggaggtca aagctatggt gagctgtgat ctcgccactg aactccagcc tggaggacaa    24540
agcaagaccc tatcaaaaaa aaaaaaaaa aaagtttct tgtgtacctg tagaatttta     24600
tctatcacat actcattatc cttttttattt taactaaaat gagatctact aaatgtattg    24660
ttctgcagct tgcttttttt aacttaatgt taatatctta tgttatcttt taacagcaca    24720
tgtagattta gatttgcttc atccttgtta agtacagctg ctagtccagt gttggaatgt    24780
gccatgctgt atgtaaccct ctcctggggg tgggcatgaa ggtggttttc tgcttttgcc    24840
cttgtaaacc atgccataat gatcatcctt gaatgccgct gtgagcatat ctgagctcca    24900
ctttaaaagt gatgcacttt tcattatact gcatgttttt taattactaa actttagttt    24960
tttagagcag ttttaggttc acagccaaat tcccgtctac cttgacccac tcgccactcc    25020
ccaggccccc gcccctggcc atgcatagcc tcccctacta tcaacatcct gcaccagaat    25080
ctgtacccac attgacacat catcatccag agtccacagt ttacatgagg gttctctctt    25140
gctgttgtac attctacata cagttacatt tgatccagag cagtgttttc ctgaaaatcc    25200
atggtttgtt tatttattta atgtatttga gacagaggct tgctctgtca cccaggcagg    25260
```

```
agtgcagtgg tgtgatctca gttcattgta acctccacct cttgggatca ggcaatcctc    25320
tcacctcagc ctcccgagta gctggaacta tgggtatgag ccaccacact tggctaattt    25380
ttaaattttt ttgtagagac agggtctaac catattgcac agtctggtct tgaactcctg    25440
gcctcaagcg atccttctgg cttggcctcc caaagtacta ggattacaga tgtgagccac    25500
tgtgccccgc tcatggtttt attttagttg ctagaaagat actatgttat cattaaaacg    25560
atctgtttga aaattggtac ttttgctgg atgcagtgac tcacgcctgt aatcccagca    25620
cttggggagg ccggtgggg aggtagatca cgaggtcagg agatcgagac catcctggct    25680
aacacggtga aacccgtct ctactaaatg tactaaaaaa attagctggg cgtggtggcg    25740
ggcacctgta gtcccagcta ctcaggaggc tgaggcagga gagtggcgtg aacccaagag    25800
gtggagcttg cagtgagctg agatcgtgcc actgcactcc agcctgggca acagagtgag    25860
actccatctc aaaaaaaaaa aaaaaaattg gtacttttta ataaaagtct ctggtttctg    25920
ggcattttaa atgtaggaat ttaatttact ttaagctcat ggaggatt tagagcgttg    25980
aaagaaatgg aaagaacaga actgggctcc ctttgtgatg tcttcagagg gaagacaagc    26040
ggagcgcgct cctgcactac ctgaaggtgt gcctgttgca tctgttttcc tttagtgcct    26100
caaaacatt gaggttggtc aggcatagaa aaagatcaga ttgttgatgc tcacacttgg    26160
agtttacaaa gcacgttccc gtacgttatc ttggtggagc ttcctggtcc ccagtgccca    26220
gcaaggcagg tggcatcatc ctggcttcac aaacaaggag agactgaggc cagagctcaa    26280
gcccagccct ctgccttgca tccagttttg gcttcctgcc cctcccctgc tctgtggtag    26340
caaaaggctc ccacacattt aagttaccag gtgttggatt tagtcagtaa cctctattat    26400
aagaaatgga tacttgaaat gtctactcct tcaggacact tcgagaggta gggctgcagt    26460
catcacctgg gggtctgctc tgggtgaggc ccttgtcctc actgtgaact tgaaagatca    26520
gtgtgacagt ttcttctcag ataagcaatc ccatctgaag accatagtct ttttctttt    26580
tttcttatct ttttttgat agattcaggg tctcactatg ttgcccaagc agtacttaaa    26640
ctcctgggct caaatgaccc tcccaccttg gtctcccaaa gtgctggaat tacaggtgtg    26700
tgctaccagc tccagtcccc ataatctttt aattcctccg attttagaat aagtcagtta    26760
taactgtaat gtgtgattcc gtttctcatt tgtccactgt ttgatggcat ccgcatgcct    26820
ggtcccatac ccgagcactg aagagcaggg tctctggagc ctggcatcgt ggggtggccc    26880
tcagcttccc cactcactgt gggaagtttc cttagtgtct ctgagcctgt ttcctcatcc    26940
gttgcctgag gataaacctg cttcaggatt gttggtgaaa agacttccct cacctagctt    27000
ctgtaacgcc actgcatgcc accactgctg agtactgttt gtttgctagg ttggtgtcat    27060
tctcatttta ccagaaagtg aagctctgag aggtcagaca gccactaaat ggcagacctg    27120
ggatttgaac ccagaactct gctcagggt caactgactg ctccccaaag gccaggtggt    27180
aaatattgca ggctttctgg gacttcagat ctctggcagc tactcaactg ttgcacctcc    27240
acaatagcta cagacagtac taaacacgca gggtggcttt gtgccagtga agctgcattt    27300
gcaaaaacag gcagcaacct ggcctcggcc ctcaggcttg tcgttgctga cctgtgtcct    27360
gtgtcttttg ttttttttt tttttgaga cagagtctct ctctgtcatc caggctgag    27420
tacagtggca cgatctgtgc tcacggcaag ctccgcctcc caggttcacg ccattctcct    27480
gcctcagcct cccaagtagc tgggactaca ggtgcccgcc accacgcctg gcttatttt    27540
tgtattttta gtagagacgg ggtttcatcg tgttagccag gatggtctcg atctcctgac    27600
cttgtgatct gccctcctcg gcttccccat gtgctgggat tacaggcgtg agccactatg    27660
```

```
cccagccccc ccgccttttt tttttttttt tttttttttt tttgagacgg agtcttgctc   27720
tctcacccag gctgaagtgc agtgacgcat ctcggctcac tgcaacctcc gcctcccggg   27780
ttcaagtgat tctcctgtct cagcctcctg aatagctggg attacaggta ctggccgcca   27840
ggcccagcta atttttgtat tttttttttt tttttttagta gaggcggggt ttcaccatgt   27900
tggtcaggct ggtcttgaaa tcctgacctc aggtgatcca cctgccttgg cgtcccagag   27960
tgttggaatt accggcatga gccactgcat ccggcttccc attgcttttt ctctgaagag   28020
actttaagac ttggagtctg gtttaaaaaa aataaagaaa taaaaatcaa tgccttctgc   28080
tggttgaacg ggaagtgtaa aatctgaatt cgctataggg tcacaatccc agcctccagt   28140
tcgcacagtg ccttcctggt gctgatgggg tgcatgttct gtcttcgcca ctaggtggag   28200
gcagttggta accttaaacc ttttgcttct cgtggttaaa agtctgacaa gaaccgtaga   28260
acctttaagc atatttaacc agtttaagcc ctgtttgcga tgttttagcc acaaagatac   28320
tgttcagtga accatttaca gttgtgcctc gcgttgtccc actctcagct gtgcatctca   28380
ctgtcgctct ggaagaccta gcccagccag tttctaggtt agcatttgaa atggtcttgg   28440
cctggtttaa ccatcagtaa atgaggccag attatgataa accttttccc ctcaaactag   28500
ggatcctctt tttctctaca atagttaaat tggaaattgt ttatgtactc tattcattta   28560
ttttggtggg tgacctgatt ttttaaattt tttagattag tcaagcacag tagtgagaag   28620
aggagaaaga gtagaacaag gtgtaactgc ctgtgaacga tcaattgaga taactcactg   28680
ccttcgacca gcagtggctt ggtttctaat gacagtaaga caagttccta tagccattgt   28740
taatctcctt ggaaaagaaa tgaacactgt gtggtttcag aagctcatta atatagcaga   28800
agcactctgc ttctgtttga agggaggttt tcagatgaat ttttctgcgt gttcattgaa   28860
cagacgtttc ctaagctcct ccttagtgcc tggcactggg aacagaagaa ggaagaagag   28920
aaagctgtgc cctcagggtg ttctcaggtc cgcactgagc ggtggtgacc agagccaccc   28980
gcctgcctgc gtggccggtg catcaggata gagcaggagt tcacagagga gctttgtcac   29040 ttcccctcc gctaaatctg ttctgtggcc ccacatcact gagtggtgtc accatcatcc   29100
agtcacctgg gacaggcagc tgggagtcat ccttgaagcc tcctcaccta ggccttcatt   29160
gcaaacctcc atttcctctg gatcactgtc accagcctag tgcaggcacc accagcttct   29220
acccagagag caggttcctt tccatctcct tctggtccca gcccagtctc tgtgcgaagg   29280
ccagaccgca gagggctcca ggccccgtga catggagttc agcgtgacct tcaggtgctg   29340
gagagagttg gcaagggctt tccatgggga actggctatg ccctgctttg cactctggac   29400
agttagcttt tgggtgctgg gcatggatcg aagggggcgca cagccggaag ggagagctgt   29460
aatcatgcag agatccttcc cctttaaagc agggacagg cgagaaagga gatcgagtca   29520
agaatggtgt ttggtgcctt tgacctcaca cttcagggt gcctcctgtg tgccatggat   29580
atcattggcc agacagggac tgatgaagac ccagccttttt taaagagtaa acaataaaca   29640
aggaaatgaa atgttcatag attgtgatag attgtatcaa tgctgcgagg gcagtaaata   29700
gaatgcggtg atagagtcaa tagaggtacc taatttgggg aggtgggggt ggtcacagat   29760
accctctctg aggggttttt gttgatgctg aaactgaagg agcaaggaac tggaaagagc   29820
tggtctctgg gtggagggag cagcccttga gctcttcctg gagcaggaga aacgtgttg   29880 tatacagtaa gggaagctcc aggtgggaga gtgataggga tgggtgtggg gagggaggtt   29940
aggctctgtg tgcagtggag aggctggtga ctacctgctg tggaggggca gagctcaggg   30000
```

```
catccatgct taagagtccc agttttggta ttatatttgc caagaaatag ccaaccggcg    30060
ggcctggagg tgcggggatg cggaaggaaa gtagtccttg agagggaatg tggtttctac    30120
ctgcacacgc acactcacat gcatacccgc ctccattacg ttgtgctgtg gttgtttttg    30180
aggcatcaga gggtgtgcgt gccgccacat gttgattggg gtggcttctg cgttcagcgc    30240
tgccgcatcc cttcacccct tccccggcact tcagaattga cacttgagct tgttgtaaa    30300 tagtgatgtg agtaactgtc attcaccgac atctccccca acacttaaag tcttagcagc    30360
tgcatttaac tcacgcatat ttgtttcatt ctaacagtgg tttctgtcac cctttgctct    30420
gcacagtttt aaaaatacct tgtaggggg cttctaagag cttggagtgc ctagtaaatg    30480
tttttgaatg gttagctaca gtgttgggtt tatatgctgt aatagtgaat ttaattggta    30540
agtaatcgtc tttctcgtca catagcccat taggatgtca ccttttctgt ttctactttg    30600
caggtcatta cacctactct gagaatcgtg tggaaaaaga cggcctgatt cttacaagcc    30660
gggggcctgg gaccagcttc gagtttgcgc ttgcaattgt tgaagccctg aatggcaagg    30720
aggtggcggc tcaagtgaag gctccacttg ttcttaaaga ctagagcagc gaactgcgac    30780
gatcacttag agaaacaggc cgttaggaat ccattctcac tgtgttcgct ctaaacaaaa    30840
cagtggtagg ttaatgtgtt cagaagtcgc tgtccttact acttttgcgg aagtatggaa    30900
gtcacaacta cacagagatt tctcagccta caaattgtgt ctatacatt ctaagccttg    30960 tttgcagaat aaacagggca tttagcaaac tactgattgt ttcttgtttt gtctctcatt    31020
tcttttgtga aattaaattc cgtatcacct tcatttgcag ctcttaactg tccatatggc    31080
actgaaataa aagaacagtg accacatttt acacagcaag gaggaaaggc atacaaacag    31140
aatttaagag gcttgtgatt ttctctgctt attagctgtg tgtttttaat gtgctattaa    31200
aaaataccaa tgagg                                                     31215

<210> SEQ ID NO 2
<211> LENGTH: 189
<212> TYPE: PRT
<213> ORGANISM: Homo sapiens

<400> SEQUENCE: 2

Met Ala Ser Lys Arg Ala Leu Val Ile Leu Ala Lys Gly Ala Glu Glu
1               5                   10                  15

Met Glu Thr Val Ile Pro Val Asp Val Met Arg Arg Ala Gly Ile Lys
            20                  25                  30

Val Thr Val Ala Gly Leu Ala Gly Lys Asp Pro Val Gln Cys Ser Arg
        35                  40                  45

Asp Val Val Ile Cys Pro Asp Ala Ser Leu Glu Asp Ala Lys Lys Glu
    50                  55                  60

Gly Pro Tyr Asp Val Val Val Leu Pro Gly Gly Asn Leu Gly Ala Gln
65                  70                  75                  80

Asn Leu Ser Glu Ser Ala Ala Val Lys Glu Ile Leu Lys Glu Gln Glu
                85                  90                  95

Asn Arg Lys Gly Leu Ile Ala Ala Ile Cys Ala Gly Pro Thr Ala Leu
            100                 105                 110

Leu Ala His Glu Ile Gly Phe Gly Ser Lys Val Thr Thr His Pro Leu
        115                 120                 125

Ala Lys Asp Lys Met Met Asn Gly Gly His Tyr Thr Tyr Ser Glu Asn
    130                 135                 140

Arg Val Glu Lys Asp Gly Leu Ile Leu Thr Ser Arg Gly Pro Gly Thr
145                 150                 155                 160
```

```
Ser Phe Glu Phe Ala Leu Ala Ile Val Glu Ala Leu Asn Gly Lys Glu
            165                 170                 175

Val Ala Ala Gln Val Lys Ala Pro Leu Val Leu Lys Asp
            180                 185

<210> SEQ ID NO 3
<211> LENGTH: 21
<212> TYPE: DNA
<213> ORGANISM: Artificial Sequence
<220> FEATURE:
<223> OTHER INFORMATION: synthetic sequence

<400> SEQUENCE: 3
cuccacuugu ucuuaaagat t                                            21

<210> SEQ ID NO 4
<211> LENGTH: 21
<212> TYPE: DNA
<213> ORGANISM: Artificial Sequence
<220> FEATURE:
<223> OTHER INFORMATION: synthetic sequence

<400> SEQUENCE: 4
ucuuuaagaa caaguggagt t                                            21

<210> SEQ ID NO 5
<211> LENGTH: 21
<212> TYPE: DNA
<213> ORGANISM: Artificial Sequence
<220> FEATURE:
<223> OTHER INFORMATION: synthetic sequence

<400> SEQUENCE: 5
cgacgaucac uuagagaaat t                                            21

<210> SEQ ID NO 6
<211> LENGTH: 21
<212> TYPE: DNA
<213> ORGANISM: Artificial Sequence
<220> FEATURE:
<223> OTHER INFORMATION: synthetic sequence

<400> SEQUENCE: 6
uuucucuaag ugaucgucgt t                                            21

<210> SEQ ID NO 7
<211> LENGTH: 21
<212> TYPE: DNA
<213> ORGANISM: Artificial Sequence
<220> FEATURE:
<223> OTHER INFORMATION: synthetic sequence

<400> SEQUENCE: 7
ggaaguaugg aagucacaat t                                            21

<210> SEQ ID NO 8
<211> LENGTH: 21
<212> TYPE: DNA
<213> ORGANISM: Artificial Sequence
<220> FEATURE:
<223> OTHER INFORMATION: synthetic sequence

<400> SEQUENCE: 8
uugugacuuc cauacuucct t                                            21
```